United States Patent
Hristov et al.

(10) Patent No.: US 11,832,933 B2
(45) Date of Patent: Dec. 5, 2023

(54) SYSTEM AND METHOD FOR WIRELESS DETECTION AND MEASUREMENT OF A SUBJECT RISING FROM REST

(71) Applicant: Emerald Innovations Inc., Cambridge, MA (US)

(72) Inventors: Rumen Hristov, Cambridge, MA (US); Zachary Kabelac, Cambridge, MA (US); Hariharan Rahul, Cambridge, MA (US); Dina Katabi, Cambridge, MA (US)

(73) Assignee: Emerald Innovations Inc., Cambridge, MA (US)

( * ) Notice: Subject to any disclaimer, the term of this patent is extended or adjusted under 35 U.S.C. 154(b) by 394 days.

(21) Appl. No.: 17/235,447

(22) Filed: Apr. 20, 2021

(65) Prior Publication Data

US 2021/0321938 A1  Oct. 21, 2021

Related U.S. Application Data

(60) Provisional application No. 63/012,730, filed on Apr. 20, 2020.

(51) Int. Cl.
*A61B 5/11* (2006.01)
*A61B 5/00* (2006.01)
(Continued)

(52) U.S. Cl.
CPC ............... *A61B 5/1118* (2013.01); *A61B 5/11* (2013.01); *A61B 5/1126* (2013.01);
(Continued)

(58) Field of Classification Search
CPC ......... A61B 5/00; A61B 5/002; A61B 5/0205; A61B 5/024; A61B 5/113; A61B 5/1115; A61B 5/1118; A61B 5/1126; A61B 5/4809; G01S 13/34; G01S 13/343; G01S 13/41; G01S 13/42; G01S 13/44; G01S 13/89;
(Continued)

(56) References Cited

U.S. PATENT DOCUMENTS 7,428,468 B2 * 9/2008 Takemura ............... G01S 17/88
702/159
9,753,131 B2 9/2017 Adib et al.
(Continued)

OTHER PUBLICATIONS

NPL Search (Jun. 16, 2023).*
(Continued)

*Primary Examiner* — Van T Trieu
(74) *Attorney, Agent, or Firm* — Intrinsic Law Corp.

(57) ABSTRACT

A method for wireless detection of a subject rising from a rest state includes producing transmitted wireless signals from one or more transmitting antennas, receiving reflected wireless signals at one or more receiving antennas, and processing the reflected wireless signals in a computer. The computer iteratively aligns candidate trajectories with a template trajectory until the current and previous template trajectories are within a predetermined distance from each other. A final template trajectory is used to determine a
(Continued)

lying-down surface exit initiation area, a lying-down surface exit initiation area exit time, a TUG plane or radius entry time, and a TUG time.

21 Claims, 11 Drawing Sheets

(51) Int. Cl.
   *G01S 7/41*  (2006.01)
   *G01S 13/34* (2006.01)
   *G01S 13/89* (2006.01)

(52) U.S. Cl.
   CPC .............. *A61B 5/4809* (2013.01); *G01S 7/41* (2013.01); *G01S 13/34* (2013.01); *G01S 13/343* (2013.01); *G01S 13/89* (2013.01)

(58) Field of Classification Search
   CPC ... G01S 7/35; G01S 7/41; G01S 7/415; G06T 5/50; G06T 15/20; G06T 15/205
   See application file for complete search history.

(56) References Cited

U.S. PATENT DOCUMENTS

| 10,746,852 | B2  | 8/2020  | Adib et al. |
| 2008/0021731 | A1* | 1/2008 | Rodgers ............. G08B 21/0469 |
| | | | 348/E7.078 |
| 2013/0100284 | A1* | 4/2013 | Fujii ........................ H04N 7/18 |
| | | | 348/135 |
| 2017/0311901 | A1 | 11/2017 | Zhao et al. |
| 2018/0271435 | A1 | 9/2018 | Zhao et al. |
| 2019/0188533 | A1 | 6/2019 | Katabi et al. |
| 2020/0341115 | A1 | 10/2020 | Katabi et al. |

OTHER PUBLICATIONS

N. B. Alexander et al., "Bed mobility task performance in older adults", Journal of Rehabilitation Research & Development, 2000, pp. 633-638, vol. 37 No. 5, Ann Arbor, MI.

Y. P. Demir et al., "Reliability and validity of Trunk Control Test in patients with neuromuscular diseases", Physiotherapy Theory and Practice, 2015, pp. 39-44, Informa Healthcare USA, Inc.

* cited by examiner

… (1) …

SYSTEM AND METHOD FOR WIRELESS DETECTION AND MEASUREMENT OF A SUBJECT RISING FROM REST

CROSS-REFERENCE TO RELATED APPLICATIONS

This application claims priority to U.S. Provisional Application No. 63/012,730, titled "System And Method For Wireless Detection And Measurement Of a Subject Rising From Rest," filed on Apr. 20, 2020, which is hereby incorporated by reference.

TECHNICAL FIELD

This application relates generally to motion tracking using wireless signals.

BACKGROUND

Wireless signals have been used to detect the presence and motion of physical bodies including living bodies, vehicles, buildings, underwater objects, and celestial bodies. Transmission and reception of wireless signals or waves is known using a variety of methods including electromagnetic and acoustic wave propagation at a range of wavelengths. Familiar examples include radar and active sonar applications.

For detection of the presence and activity of a human subject, certain considerations are in order. One aspect benefiting from detection and measurement of the dynamics of a human subject is in the context of timed-up-and-go (TUG) measurements, which generally determines the length of time required for a subject to get up from a seated position and commence upright locomotion. Typically, the TUG is considered to be the time from when the subject commences getting up from a seated position until the subject reaches a set distance (e.g., 2 to 4 meters) from the place where he or she was seated. Such measurements are clinically related to a subject's neurological, musculoskeletal, cardiovascular health and other conditions and diseases. Conclusions regarding the subject's balance, lower and abdominal strength and gait are related to the subject's TUG. An optimized TUG (O-TUG) is considered to be the time from when the subject commences getting up from a prone position until the subject reaches a set distance. TUG and O-TUG are used interchangeably herein.

Traditionally, a practitioner or human observer in a clinical setting will time the subject, e.g., using a clock or stop-watch, and actively measure the TUG of a subject who performs the measured activity on command, such as getting up out of a chair and walking a determined distance.

In addition to being resource intensive, performing laboratory measurements of TUG using a professional observer is prone to human errors and other systematic errors insofar as the subject and the person performing the measurement may affect the measurement through their own bias in the context of a deliberate measurement. For example, the subject may artificially exert themselves in an unnatural way due to being observed at home or in a clinical setting by another. Also, the amount of data collected in human-measured clinical or laboratory or other settings is limited because of the effort required to take the subject to the clinic, lab, or to bring the observer to the home of the subject. Thus, data collection using human observers recording TUG time is not ideal as there are only so many natural movements the subject will perform for the sake of measurement, and the lack of repetition of natural getting up cycles would result in a small collected data set.

Automation of the TUG measurements can be conceived, for example if a camera is trained on the chair used by the subject. But using optical imaging methods (e.g., cameras) pose yet other challenges such as privacy concerns since a person whose TUG is under study may not appreciate a camera or cameras capturing and storing and sending images of their activity at home, in their bedroom, and so on.

SUMMARY

Example embodiments described herein have innovative features, no single one of which is indispensable or solely responsible for their desirable attributes. The following description and drawings set forth certain illustrative implementations of the disclosure in detail, which are indicative of several example ways in which the various principles of the disclosure may be carried out. The illustrative examples, however, are not exhaustive of the many possible embodiments of the disclosure. Without limiting the scope of the claims, some of the advantageous features will now be summarized. Other objects, advantages and novel features of the disclosure will be set forth in the following detailed description of the disclosure when considered in conjunction with the drawings, which are intended to illustrate, not limit, the invention.

An aspect of the invention is directed to a method for wireless detection of a subject rising from a rest state, comprising: a. producing transmitted wireless signals from one or more transmitting antennas; b. receiving reflected wireless signals at one or more receiving antennas, the reflected wireless signals being reflected from the subject partially or fully; c. processing the reflected wireless signals in a computer to estimate a lying-down area of the subject, the computer including a microprocessor and memory electrically coupled to the microprocessor; d. processing the reflected wireless signals in the computer to determine a plurality of candidate trajectories of the subject, each candidate trajectory corresponding to a movement of the subject over a time period; e. aligning the candidate trajectories, in the computer, with an initial template trajectory; f. determining, in the computer, a new template trajectory using the aligned candidate trajectories; and g. determining, in the computer, whether the new template trajectory is within a predetermined distance of the initial template trajectory. The method further comprises h. when the new template trajectory is greater than the predetermined distance of the initial template trajectory: replacing the new template trajectory with the initial template trajectory; and repeating steps e-g until the new template trajectory is within the predetermined distance of the initial template trajectory. The method further comprises i. when the new template trajectory is less than or equal to the predetermined distance of the initial template trajectory: saving the new template trajectory as a final template trajectory; determining, in the computer, a lying-down surface exit initiation area using the aligned candidate trajectories; determining, in the computer, a lying-down surface exit initiation area exit time for each aligned candidate trajectory using the lying-down surface exit initiation area; determining, in the computer, a TUG plane entry time for each aligned candidate trajectory; and calculating, in the computer, a TUG time based on a difference between the TUG plane entry time and the lying-down surface exit initiation area exit time.

In one or more embodiments, the one or more transmitting antennas are configured to transmit wireless signals having a wavelength greater than 1 mm. In one or more embodiments, the one or more transmitting antennas comprise a plurality of the transmitting antennas, the one or more receiving antennas comprise a plurality of the receiving antennas, and the transmitting and receiving antennas are arranged along two orthogonal axes. In one or more embodiments, the transmitting antennas and the receiving antennas are evenly spaced along the two orthogonal axes.

In one or more embodiments, the method further comprises determining whether the candidate trajectories satisfy one or more predefined trajectory requirements. In one or more embodiments, the predefined trajectory requirement(s) include that the candidate trajectory originates at a lying-down surface. In one or more embodiments, the predefined trajectory requirement(s) include that the candidate trajectory extends away from the lying-down surface. In one or more embodiments, the predefined trajectory requirement(s) include that the candidate trajectory remains on the lying-down surface for less than a predetermined maximum time period.

In one or more embodiments, the step of determining a lying-down surface exit initiation area exit time using the final template trajectory and the lying-down surface exit initiation area, comprises determining a time stamp at which each aligned candidate trajectory moves in a same direction. In one or more embodiments, the step of determining a time stamp at which each aligned candidate trajectory moves in a same direction comprises: computing a sum of displacement vectors for the aligned candidate trajectories at respective timestamps; and selecting a first timestamp where a magnitude of the sum of the displacement vectors is greater than a threshold value.

Another aspect of the invention is directed to a system for wireless detection of a subject rising from a rest state, comprising: one or more transmitting antennas; one or more receiving antennas; a microprocessor electrically coupled to the one or more transmitting and the one or more receiving antennas; a power supply electrically coupled to the microprocessor; and computer-readable memory electrically coupled to the microprocessor, the computer-readable memory including computer-readable instructions that, when executed by the microprocessor, cause the microprocessor to: a. produce transmitted wireless signals from the one or more transmitting antennas; b. receive reflected wireless signals from the one or more receiving antennas, the reflected wireless signals being reflected from the subject partially or fully; c. process the reflected wireless signals to estimate a lying-down area of the subject; d. process the reflected wireless signals to determine a plurality of candidate trajectories of the subject, each candidate trajectory corresponding to a movement of the subject over a time period; e. align the candidate trajectories with an initial template trajectory; f. determine a new template trajectory using the aligned candidate trajectories; and g. determine whether the new template trajectory is within a predetermined distance of the initial template trajectory. The computer-readable instructions further cause the microprocessor to h. when the new template trajectory is greater than the predetermined distance of the initial template trajectory: replace the new template trajectory with the initial template trajectory; and repeat steps e-g until the new template trajectory is within the predetermined distance of the initial template trajectory. The computer-readable instructions further cause the microprocessor to i. when the new template trajectory is less than or equal to the predetermined distance of the initial template trajectory: save the new template trajectory as a final template trajectory; determine a lying-down surface exit initiation area using the aligned candidate trajectories; determine a lying-down surface exit initiation area exit time for each aligned candidate trajectory using the lying-down surface exit initiation area; determine a TUG plane entry time for each aligned candidate trajectory; and calculate a TUG time based on a difference between the TUG plane entry time and the lying-down surface exit initiation area exit time.

In one or more embodiments, the system further comprises a communication port operatively coupled to the microprocessor. In one or more embodiments, the communication port is configured to communicate with an external device over a communication network. In one or more embodiments, the one or more transmitting antennas comprise a plurality of the transmitting antennas, the one or more receiving antennas comprise a plurality of the receiving antennas, and the transmitting and receiving antennas are arranged along two orthogonal axes. In one or more embodiments, the transmitting antennas and the receiving antennas are evenly spaced along the two orthogonal axes.

Another aspect of the invention is directed to a method for wireless detection of a subject rising from a rest state, comprising: producing transmitted wireless signals from one or more transmitting antennas; receiving reflected wireless signals at one or more receiving antennas, the reflected wireless signals being reflected partially or fully from the subject while the subject transitions from a lying-down position on a platform to a travelling position; processing the reflected wireless signals in a computer to repeatably measure a position of the subject; identifying, with the computer, a change in the position of the subject that initiates a transition to leave the platform; starting a TUG timer, with the computer, when the subject initiates the transition to leave the platform; and stopping the TUG timer, with the computer, when the subject (a) has travelled a predetermined distance from the platform, (b) has travelled from the platform along a predetermined trajectory for a predetermined time period, or (c) has reached a predetermined location, the predetermined location comprising an absolute location or a relative location with respect to the platform, wherein the TUG timer indicates a TUG time.

In one or more embodiments, the change in the position of the subject that initiates the transition to leave the platform is related to a position of the subject entering a pre-determined exit initiation area. In one or more embodiments, the method further comprises determining a quantified measure of a disease severity, a disease progression, and/or a medication effectiveness using the TUG time. In one or more embodiments, the one or more transmitting antennas comprise a plurality of the transmitting antennas, the one or more receiving antennas comprise a plurality of the receiving antennas, and the transmitting and receiving antennas are arranged along two orthogonal axes. In one or more embodiments, the method further comprises stopping the TUG timer only when (a) a measured trajectory of the subject follows a straight path or (b) the subject moves along the measured trajectory at a consistent pace.

BRIEF DESCRIPTION OF THE DRAWINGS

For a fuller understanding of the nature and advantages of the present concepts, reference is made to the detailed description of preferred embodiments and the accompanying drawings.

DETAILED DESCRIPTION

A wireless motion tracking system is used to monitor the position of a subject during rest and when the subject rises from rest to non-invasively determine the subjects' TUG time. The wireless motion tracking system uses RF signals, ultrasound signals, or other energy signals to determine the subject's position without using a camera or other optics that may be perceived as invasive to the subject's privacy. The wireless motion tracking system can include RF transmitting antennas and receiving antennas, which can be disposed in one or more arrays. The received signals are processed by a microprocessor to automatically determine the subject's location.

Figure 1:
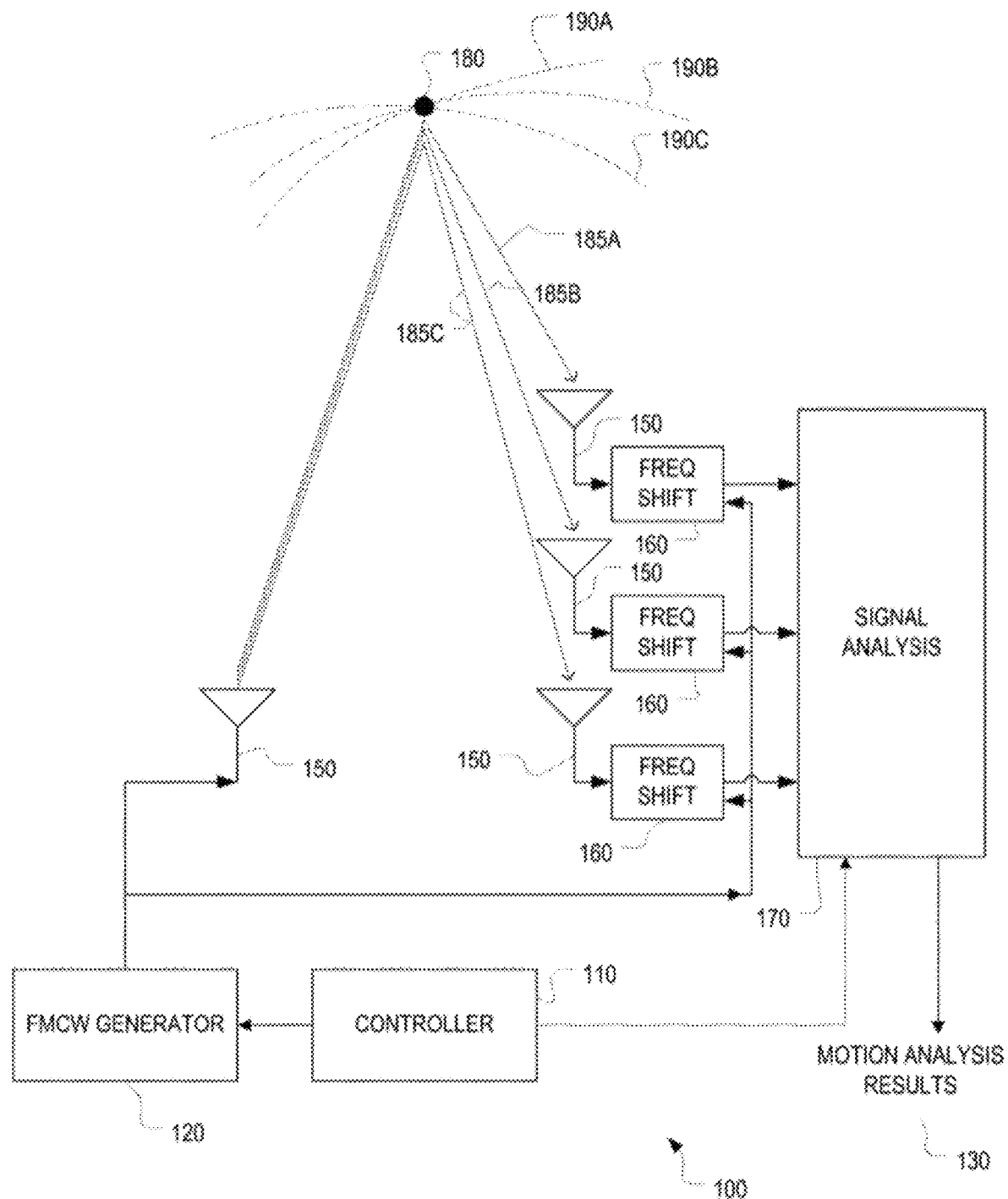
FIG. 1 is a block diagram of a motion tracking system according to an embodiment.

Referring to FIG. 1, a first embodiment of a motion tracking system 100 makes use of a number antennas 150 to transmit and receive radio frequency signals that are reflected, partially or fully, from objects (e.g., people) in the environment of the system 100, which may include one or more rooms of a building, the interior of a vehicle, etc., and may be partitioned, for example, by substantially radio-transparent barriers, for instance building walls or cloth sheets. In general, the objects in the environment include both fixed objects, such as chairs, walls, etc., as well as moving objects, such as but not limited to people. The system 100 can track people, who may be moving around a room, getting out of a sleep platform (e.g. bed), or may be relatively stationary, for instance, sitting in a chair or lying in bed, but may nevertheless exhibit breathing motion that may be detected by one or more embodiments described below. The system 100 provides motion analysis results 130 based on the radio frequency signals. In various embodiments, these results include locations of one or more people in the environment, detected body or limb gestures made by the people in the environment, and detected physical activity including detection of falls.

Generally, the system 100 makes use of time-of-flight (TOF) (also referred to as "round-trip time") information derived for various pairs of antennas 150. For schematic illustration in FIG. 1, three paths 185A-C reflecting off a representative point object 180 are shown between a transmitting antenna 150 and three receiving antennas 150, each path generally having a different TOF. Assuming a constant signal propagation speed c (i.e., the speed of light), the TOF from an antenna at coordinates $(x_t, y_t, z_t)$ reflecting from an object at coordinates $(x_o, y_o, z_o)$ and received at an antenna at coordinates $(x_r, y_r, z_r)$ can be expressed as:

$$\frac{1}{c}\left(\sqrt{(x_t-x_o)^2+(y_t-y_o)^2+(z_t-z_o)^2} + \sqrt{(x_r-x_o)^2+(y_r-y_o)^2+(z_r-z_o)^2}\right).$$

For a particular path, the TOF, for example associated with path 185A, constrains the location of the object 180 to lie on an ellipsoid defined by the three-dimensional coordinates of the transmitting and receiving antennas of the path, and the path distance determined from the TOF. For illustration, a portion of the ellipsoid is depicted as the elliptical line 190A. Similarly, the ellipsoids associated with paths 185B-C are depicted as the lines 190B-C. The object 180 lies at the intersection of the three ellipsoids.

Continuing to refer to FIG. 1, the system 100 includes a signal generator that generates repetitions of a signal pattern that is emitted from the transmitting antenna 150. In this embodiment, the signal generator is an ultra-wide band frequency modulated carrier wave (FMCW) generator 120. It should be understood that in other embodiments other signal patterns and bandwidth(s) than those described herein may be used while following other aspects of the described embodiments.

Additional details regarding the motion tracking systems, methods, and/or other aspects of this disclosure are described in the following documents, which are hereby incorporated by reference: U.S. Pat. No. 9,753,131, titled "Motion Tracking Via Body Radio Reflections," which issued on Sep. 5, 2017; U.S. Patent Application Publication No. 2020/0341115, titled "Subject identification in behavioral sensing systems," which published on Oct. 29, 2020; U.S. Patent Application Publication No. 2019/0188533, titled "Pose Estimation," which published on Jun. 20, 2019; U.S. Patent Application Publication No. 2018/0271435, titled "Learning Sleep Stages From Radio Signals," which published on Sep. 27, 2018; and/or U.S. Patent Application Publication No. 2017/0311901, titled "Extraction Of Features From Physiological Signals," which published on Nov. 2, 2017.

Figure 2A:
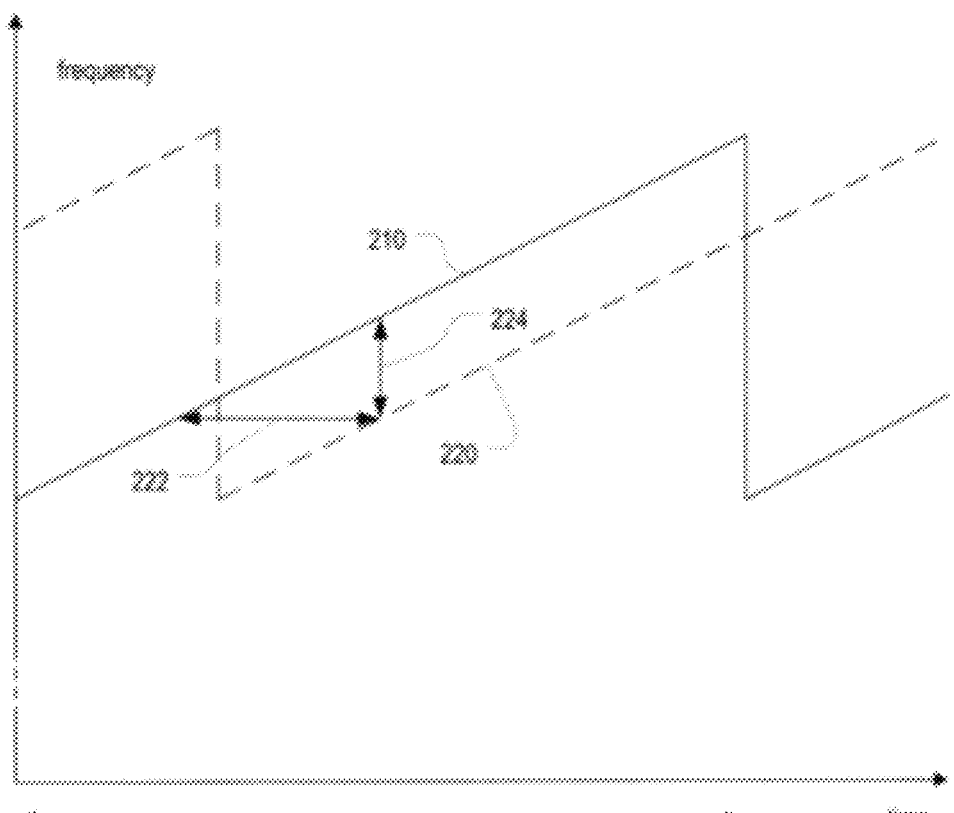
FIG. 2A is a plot of transmit and receive frequencies with respect to time.

Referring to FIG. 2A, TOF estimates are made using a frequency-modulated carrier wave (FMCW) approach. Considering a single transmit and receive antenna pair, in each of a series of repeating time intervals 212 of duration T, a transmit frequency is swept from over a frequency range as shown by solid line 210. In some embodiments, the frequency range is about 5.46-7.25 GHz (i.e., a frequency range of about 1.8 GHz) with a sweep duration and repetition rate of about 2.5 milliseconds. The receiving antenna receives the signal after a TOF 222 (i.e., reflected from a single object), with frequency as shown in the dashed line 220. Note that the TOF 222 corresponds to a difference 224 in transmitted and received frequencies, which is a product of the TOF and the rate of frequency change of the swept carrier for the transmit antenna.

Figure 2B:
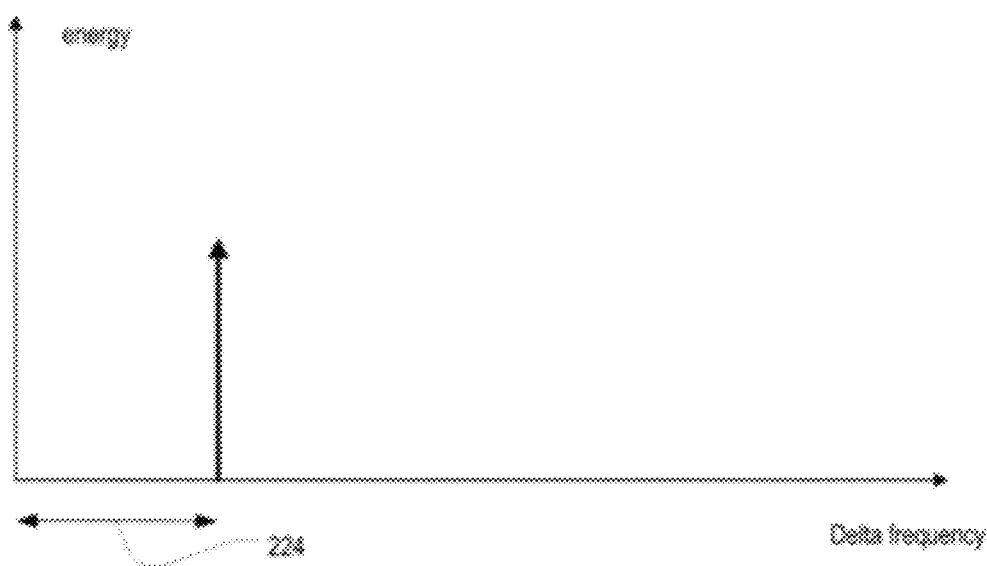
FIG. 2B is a plot of received energy with respect to frequency corresponding to FIG. 2A.

Referring to FIG. 2B, if the received reflected signal (dashed line 220 in FIG. 2A) is frequency-shifted according to transmitted signal (solid line 210 in FIG. 2A), then the result will have energy concentrated at the frequency difference 224 corresponding to the TOF. Note that we are ignoring the edges of the intervals 212, which are exaggerated in the figures. Referring back to FIG. 1, a frequency shift component 160 (also referred to as a "downconverter" or a "mixer") implements the frequency shifting, for example, including a modulator that modulates the received signal with the transmitted signal and retaining a low frequency range representing TOF durations that are consistent with the physical dimensions of the environment.

The output of the frequency shifter is subject to a spectral analysis (e.g., a Fourier transform) to separate the frequency components each associated with a different TOF. In this embodiment, the output of the frequency shifter is sampled and a discrete time Fourier transform implemented as a fast Fourier transform (FFT) is computed for each interval 212. Each complex value of the FFT provides a frequency component with a frequency resolution $\Delta f = n/T_{sweep}$ where $T_{sweep}$ is the sweep duration (e.g., 2.5 milliseconds) and n is the number of samples per sweep.

Continuing to refer to FIG. 2B, it should be recognized that the distribution of energy over frequency (and equivalently over TOF), is not generally concentrated as shown in this figure. Rather, there is a distribution of energy resulting from the superposition of reflections from the reflective objects in the environment. Some reflections are direct, with the path being direct between the reflecting object and the transmitting and receiving antennas. Other reflections exhibit multipath effects in which there are multiple paths from a transmitting antenna to a receiving antenna via a particular reflecting object. Some multipath effects are due to the transmitted signal being reflected off wall, furniture, and other static objects in the environment. Other multipath effects involve reflection from a moving body, where the path is not direct from the transmitting antenna to a moving object and back to the receiving antenna, but rather is reflected from one or more static objects either on the path from the transmitting antenna to the moving object or from the moving object back to the receiving antenna, or both.

The system 100 addresses the first multipath effect, referred to as static multipath, using a time-differencing approach to distinguish a moving object's reflections from reflections off static objects in the environment, like furniture and walls. Typically, reflections from walls and furniture are much stronger than reflections from a human, especially if the human is behind a wall. Unless these reflections are removed, they would mask the signal coming from the human and prevent sensing her motion. This behavior is called the "Flash Effect".

To remove reflections from all of these static objects (e.g., walls, furniture), we leverage the fact that since these reflectors are static, their distance to the antenna array does not change over time, and therefore their induced frequency shift stays constant over time. We take the FFT of the received signal every sweep window and eliminate the power from these static reflectors by subtracting the (complex) output of the FFT in a given sweep from the FFT of the signal in a previous sweep. This process is called background subtraction because it eliminates all the static reflectors in the background. In some embodiments, the immediately-previous sweep (i.e., 2.5 milliseconds previous) is background subtracted, while in other embodiments, a greater delay may be used (e.g., 12.5 milliseconds, or even over a second, such as 2.5 seconds) to perform background subtraction.

By eliminating all reflections from static objects, the system is ideally left only with reflections from moving objects. However, as introduced above, these reflections include both signals that travel directly from the transmitting antenna to the moving body (without bouncing off a static object), reflect of the object, and then travel directly back to the receiving antenna, as well as indirect paths that involve reflection from a static object as well as form a moving object. We refer to these indirect reflections as dynamic multi-path. It is quite possible that moving object reflection that arrives along an indirect path, bouncing off a side wall, is stronger than her direct reflection (which could be severely attenuated after traversing a wall) because the former might be able to avoid occlusion.

The general approach to eliminating dynamic multi-path is based on the observation that, at any point in time, the direct signal paths to and from the moving object has travelled a shorter path than indirect reflections. Because distance is directly related to TOF, and hence to frequency, this means that the direct signal reflected from the moving object would result in the smallest frequency shift among all strong reflectors after background subtraction. We can track the reflection that traveled the shortest path by tracing the lowest frequency (i.e., shorted time of flight) contour of all strong reflectors.

Figure 3A:
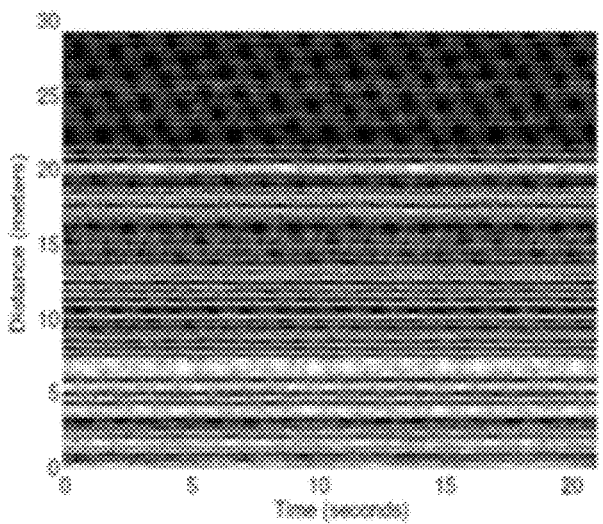
FIG. 3A is a spectrogram (spectral profile versus time) for one transmit and antenna pair.
Figure 3B:
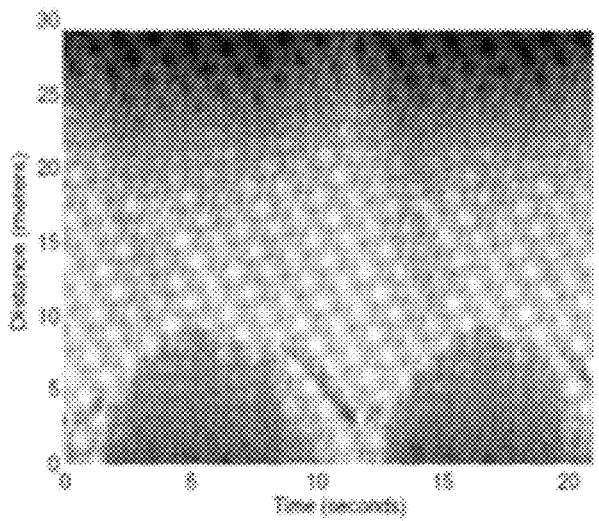
FIG. 3B is the spectrogram of FIG. 3A after background subtraction.
Figure 3C:
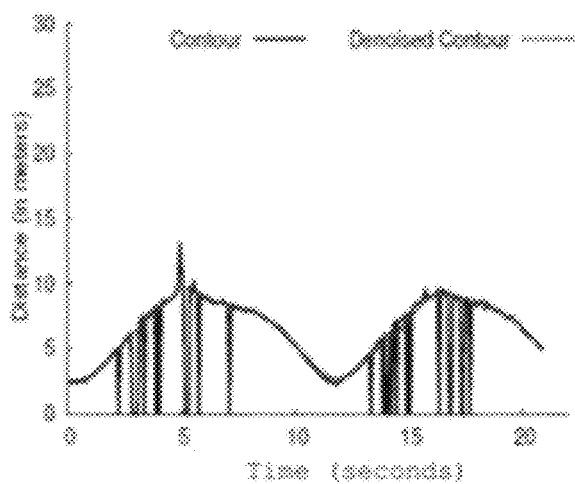
FIG. 3C is a plot of estimates of a first round trip time corresponding to the spectrogram in FIG. 3B.

Referring to FIGS. 3A-C, the horizontal axis of each figure represents a time interval of approximately 20 seconds, and the vertical axis represents a frequency range corresponding to zero distance/delay at the bottom to a frequency corresponding to a range of approximately 30 meters at the top. FIGS. 3A and 3B show FFT power before background subtraction (FIG. 3A) and after background subtractions (FIG. 3B). Fig FIG. 3C shows the successive estimates of the shortest distance (or equivalently time) of flight for successive sweeps, as well as a "denoised" (e.g., smoothed, outlier eliminated, etc.) contour.

To determine the first local maximum that is caused by a moving body, we must be able to distinguish it from a local maximum due to a noise peak. We achieve this distinguishability by averaging the spectrogram across multiple sweeps. In this embodiment, we average over five consecutive sweeps, which together span a duration of 12.5 milliseconds, prior to locating the first local maximum of the FFT power. For all practical purposes, a human can be considered as static over this time duration; therefore, the spectrogram (i.e., spectral distribution over time) would be consistent over this duration. Averaging allows us to boost the power of a reflection from a moving body while diluting the peaks that are due to noise. This is because the human reflections are consistent and hence add up coherently, whereas the noise is random and hence adds up incoherently. After averaging, we can determine the first local maximum that is substantially above the noise floor and declare it as the direct path to the moving body (e.g., a moving human).

In practice, this approach using the first reflection time rather than the strongest reflection proves to be more robust, because, unlike the contour which tracks the closest path between a moving body and the antennas, the point of maximum reflection may abruptly shift due to different indirect paths in the environment or even randomness in the movement of different parts of a human body as a person performs different activities.

Note that the process of tracking the contour of the shortest time of flight is carried out for each of the transmitting and receiving antenna pairs, in this embodiment, for the three pairs each between the common transmitting antenna and the three separate receiving antennas. After obtaining the contour of the shortest round-trip time for each receive antenna, the system leverages common knowledge about human motion to mitigate the effect of noise and improve its tracking accuracy. The techniques used include outlier rejection, interpolation, and/or filtering.

In outlier rejection, the system rejects impractical jumps in distance estimates that correspond to unnatural human motion over a very short period of time. For example, in FIG. 3C, the distance from the object repeatedly jumps by more than 5 meters over a span of few milliseconds. Such changes in distance are not possible over such small intervals of time, and hence the system rejects such outliers.

In interpolation, the system uses its tracking history to localize a person when she stops moving. In particular, if a person walks around in a room then sits on a chair and remains static, the background-subtracted signal would not register any strong reflector. In such scenarios, we assume that the person is still in the same position and interpolate the latest location estimate throughout the period during which we do not observe any motion, enabling us to track the location of a subject even after she stops moving.

In filtering, because human motion is continuous, the variation in an object's distance to each receive antenna should stay smooth over time. Thus, the system uses a filter, such as a Kalman filter, to smooth the distance estimates.

After contour tracking and de-noising of the estimate, the system obtains a clean estimate of the distance travelled by the signal from the transmit antenna to the moving object, and back to one of the receive antennas (i.e., the round trip distance). In this embodiment that uses one transmitting antenna and three receiving antenna, at any time, there are three such round trip distances that correspond to the three receive antennas. The system uses these three estimates to identify the three-dimensional position of the moving object, for each time instance.

The system leverages its knowledge of the placement of the antennas. In this embodiment, the antennas are placed in a "T" shape, where the transmitting antenna is placed at the cross-point of the "T" and the receiving antennas are placed at the edges, with a distance of about 1 meter between the transmitting antenna and each of the receiving antennas. For reference, the z axis refers to the vertical axis, the x axis is along the horizontal, and with the "T" shaped antenna array mounted to a wall the y axis extends into the room. Localization in three dimensions uses the intersection of the three ellipsoids, each defined by the known locations of the transmitting antenna and one of the receiving antennas, and the round-trip distance.

Note that in alternative embodiments, only two receiving antennas may be used, for example with all the antennas placed along a horizontal line. In such an embodiment, a two-dimensional location may be determined using an intersection of ellipses rather than an intersection of ellipsoids. In other alternative embodiments, more than three receiving antennas (i.e., more than three transmitting-receiving antenna pairs) may be used. Although more than three ellipsoids do not necessarily intersect at a point, various approaches may be used to combine the ellipsoids, for example, based on a point that is closest to all of them.

For example, the antennas can include an antenna array in which antenna elements are distributed in two dimensions. A particularly useful embodiment is an antenna array in which antenna elements are arranged at regular intervals along vertical and horizontal axes. This arrangement can provide a particularly convenient way to separate signals that come from different locations in the three-dimensional space.

A frame generator can process the data that arrives from the receiving antennas to form RF frames or "frames." The frame generator can use the antenna elements along the horizontal axis to generate successive two-dimensional horizontal frames and can use the antenna elements along the vertical axis to generate successive two-dimensional vertical frames. The horizontal frames are defined by a distance axis and a horizontal-axis. The vertical frames are defined by the same distance axis and a vertical-angle axis. The horizontal and vertical frames can therefore be viewed as projections of the frame into two subspaces.

The frame generator can generate data indicative of a reflection from a particular distance and angle. It does so by evaluating a double-summation for the horizontal frames and another double-summation for the vertical frames.

The double-summations are identical in form and differ only in details related to the structures of the horizontal and vertical lines of antennal elements and in whether the vertical or horizontal angle is being used. Thus, it is sufficient to show only one of the double summations below:

$$P(d, \theta) = \sum_{n=1}^{N} \sum_{t=1}^{T} s_{n,t} e^{j2\pi k dt/c} e^{j2\pi n \cos(\theta)/\lambda}$$

In the foregoing double summation, $P(d, \theta)$ represents the value of the reflection from a distance in the direction $\theta$, $s_{n,t}$ represents the $t^{th}$ sample of the reflected chirp (e.g., transmitted signal pattern) as detected by the nth antenna element in the line of antenna elements, c and $\lambda$ represent the radio wave's velocity and its relevant wavelength, respectively, N represents the total number of antenna elements in the relevant axis of antenna elements, T represents the number of samples from the relevant reflection of the outgoing chirp, I represents the spatial separation between adjacent antenna elements, and k represents the slope of the chirp in the frequency domain.

As a result, at each step, it is possible to represent the reflected signal using its projection on a horizontal plane and on a vertical plane. The horizontal frame captures information concerning a subject's location and the vertical frame captures information concerning the subject's build, including such features as the subject's height and girth. Differences between successive frames in a sequence of horizontal and vertical frames can provide information concerning each subject's characteristic gait and manner of movement. A preferred embodiment operates at a frame rate of thirty frames-per-second. This is sufficient to assume continuity of locations. Additional details regarding the antenna arrangement and frame calculation are disclosed in U.S. Patent Application Publication No. 2020/0341115.

Figure 4:
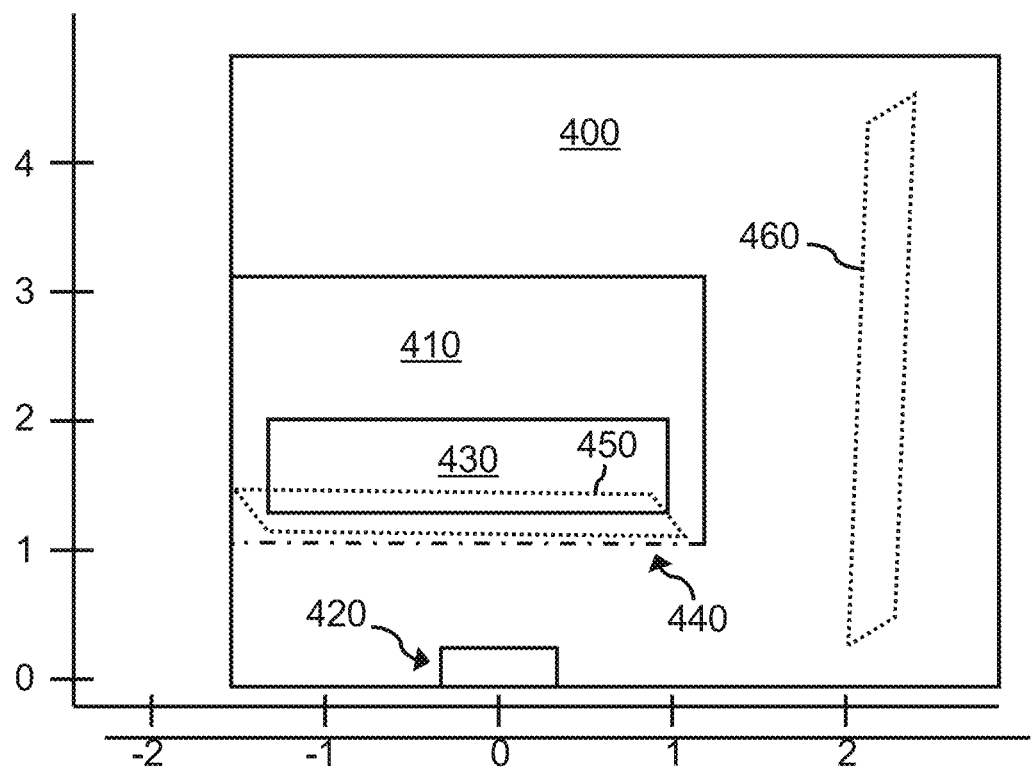
FIG. 4 is a block diagram of an example room or other indoor environment in which embodiments of the invention can be applied.

FIG. 4 is a block diagram of an example room 400 or other indoor environment in which embodiments of the invention can be applied. A typical home or institution or hospital room may be the general space within which most or all of the present steps are carried out. The room 400 includes a bed 410 or other sleep platform and a wireless motion tracking system 420 disposed at the (0, 0) reference location, where the numbers along the two axes are indicated in meters. The wireless motion tracking system 420 can be the same as system 100 in some embodiments. The area and position of the walls of the room and its contents, including the bed 410 or other furnishings, can be automatically measured by the wireless motion tracking system 420, or can be entered manually such as at the time of installation of the system to identify or key in the relative dimensions or locations of key objects such as walls, beds, and so on.

The subject lies on the bed 410 in a sleep or lying-down area 430, which can encompass the whole bed 410 or a portion of the lying surface of the bed 410, for example if the subject sleeps or lies down on one side of the bed 410 or shares the bed 410 with a partner or a pet. In one aspect, the wireless motion tracking system 420 can recognize that human subjects generally arise from bed in a similar way each day. Typically, the subject would wake up, move around some, and then at the time he or she decides to arise, the subject moves to a given side of the bed 410, which can be referred to as a bed exit initiation area 440 because it initiates the getting-out-of-bed process. Therefore, pre-getting up time and movements of the subject are not determined or analyzed, at least in some embodiments, as they are not as relevant to the subject's TUG measurement. A start time is determined when the subject has apparently decided to actively get up out of bed 410, and which is associated with moving into and then out of the initiation area 440 of the bed 410, typically the subject's "side" of the bed 410 when the subject shares the bed 410 with another person or animal. Bed exit initiation area 440 can also be referred to as a lying-down surface exit initiation area.

Through data collection, observation, and analysis, the present system and method can determine or estimate an initiation time when the subject actively (e.g., observably) intends to and commences the bed exit process (e.g., a lying-down surface exit initiation area exit time). An exit plane 450 or region can be identified as shown, which may be a line or a plane that is crossed when the subject exits the bed 410. The exit plane 450 can pass through or can be disposed adjacent to the initiation area 440. All throughout the process of waking up and getting up, the present system uses its transceiver array of antennas or transducers to repeatably detect and measure the position of the subject and to determine, using the techniques outlined herein, whether the subject has gotten up out of bed and the amount of time required to leave the bed area and travel a predetermined distance (e.g., the TUG time). A TUG plane 460 or line can be used to define the predetermined distance (e.g., 2-4 meters) for the subject to walk to determine the TUG time. The exit plane 450 and the TUG plane 460 can be manually entered into the system (e.g., into the wireless motion tracking system 420) or can be determined automatically by the system. Alternatively, a TUG radius (e.g., 2-4 meters) can be used to define the predetermined distance.

A large number of position measurements may be collected by the system over time. The system, unlike a human observer, can detect and log data for a long period of time, for example to assess the sleeping or lying-down position and movements of a subject under observation over the period of a night's sleep or over a period of several or many days. The data collected can include position information representing the subject's position with respect to a reference position (for example the present device's (0, 0) position as defined, but this is not limiting as would be appreciated by those skilled in the art). A graphical representation of the acquired subject position data can be generated as a heatmap, for example as illustrated in FIGS. 5A and 5B.

Though the invention is described with respect to an indoor environment, it can also be carried out in other environments such as outdoor environments, holding areas, vehicles, and so on without loss of generality.

Figure 5A:
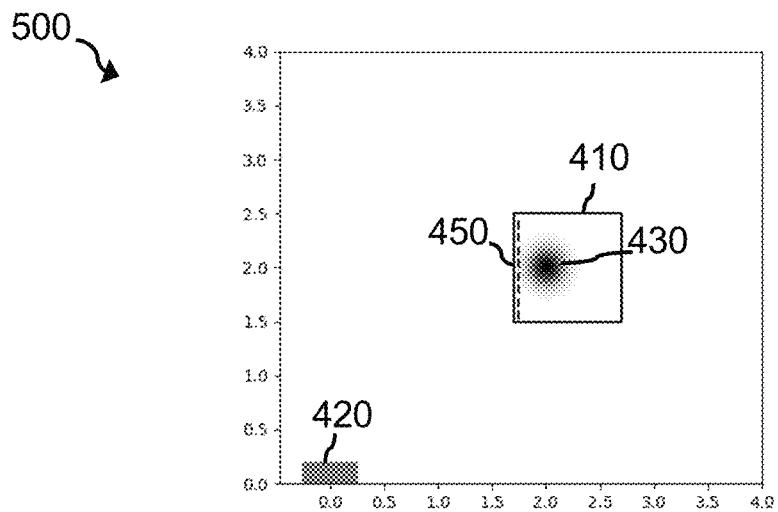
FIGS. 5A and 5B are heatmaps of the accumulated position data indicating that the subject is located at a certain sleep area of the bed for the majority of the observation time.
Figure 5B:
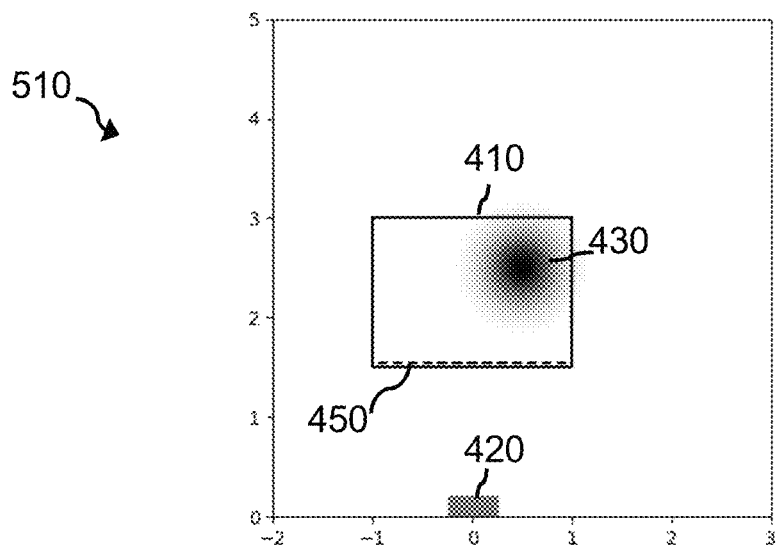

FIGS. 5A and 5B are heatmaps 500, 510, respectively, of the accumulated position data indicating that the subject is located at a certain sleep area (e.g., sleep or lying-down area 430) of the bed (e.g., bed 410) or platform for the majority of the observation time. The wireless motion tracking system 420 can therefore observe and locate the subject during his or her sleep and determine the subject's sleep or lying-down area.

Conclusions can be drawn regarding the subject's sleep pattern and health from the aggregated position data, for example indicating how much the subject moves around in the sleep or lying-down area during a night's sleep or from night to night. One beneficial aspect of the invention is that it can collect sufficient data and automatically analyze the same so as to determine, with greater accuracy and effectiveness than prior methods, the beginning of a subject's effort or active intent to get up out of bed, and can then start measuring the subject's bed exit time TUG. In an example, the TUG measurement can commence when the system detects the subject entering into the initiation area 440 of the bed 410 or crossing exit plane 450 through which the subject typically exits the bed 410.

Figure 6A:
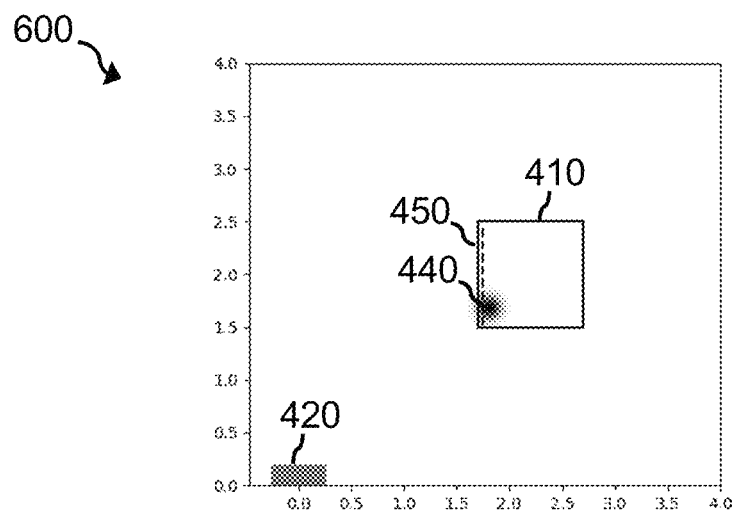
FIGS. 6A and 6B are heatmaps of the accumulated position data of a subject's entry into his or her initiation area, which can be defined in one, two, or more dimensions with respect to a reference point.
Figure 6B:
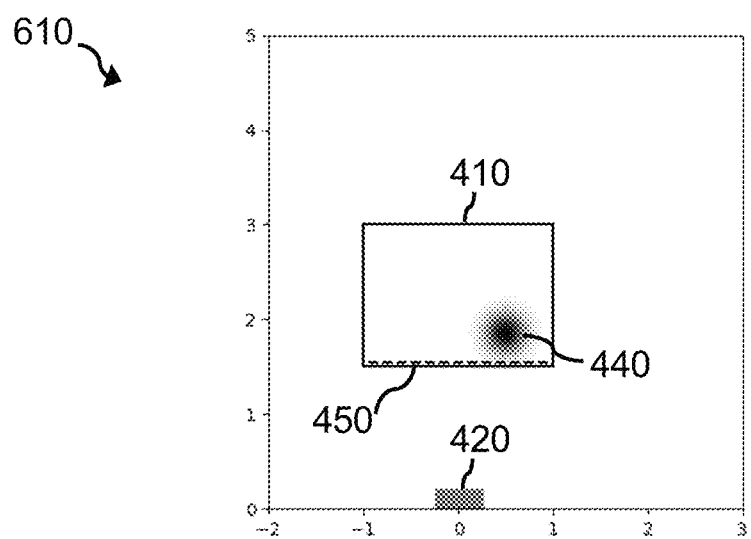

FIGS. 6A and 6B are heatmaps 600, 610, respectively, of the accumulated position data of a subject's entry into his or her initiation area 440, which can be defined in one, two, or more dimensions with respect to a reference point. The initiation area 440 and/or exit plane 450 may be used to indicate the entry of the subject into a spatial zone where getting up and out of bed 410 occurs. Though a subject's entry into the initiation area 440 may vary over time, a general pattern can be described or inferred by the system as most people get out of the bed 410 using the same or nearly same initiation area 440 every time. Again, a line or a plane, such as exit plane 450, can be defined where the subject's actual exit from bed 410 is defined, e.g., at the edge of the bed 410 by the initiation area 440 or thereabouts.

In some embodiments, the movement of the subject is studied in two dimensions (x, y) lying in a plane of or parallel to the surface of the bed 410 or surface on which the subject lies or parallel to the floor. However, in other embodiments or optional features, a third dimension (z) may be measured and computations are performed in three dimensions. Therefore, any examples shown in two dimensions can be extended to three dimensions (x, y, z) by extension if elevation data (z) is collected by the measurement transceiver system.

Any system of coordinates may be used to describe the objects and subject in the environment, including Cartesian coordinates, spherical coordinates, cylindrical coordinates, or others. Those skilled in the art will also understand that the definition of the origin point or reference location can be modified as suits a certain application and is not limited to centering the coordinate system about the system's transceiver device 420, but could equally be referenced to the center of the subject's bed, the bed exit point, or another location. In addition, the coordinate system does not necessarily need to be based on a stationary or "laboratory" frame of reference, but if desired may be based on a position that moves with a subject of interest (e.g., akin to using a Lagrangian or a Hamiltonian frame of reference).

In some embodiments, the breathing, heart rate or sleep behavior of the subject might be monitored and recorded or reported in addition to the trajectory information. Such information may, in some aspects, augment the tracking information to enable detection of when the subject starts moving, and when the subject is no longer present in the bed.

Figure 7:
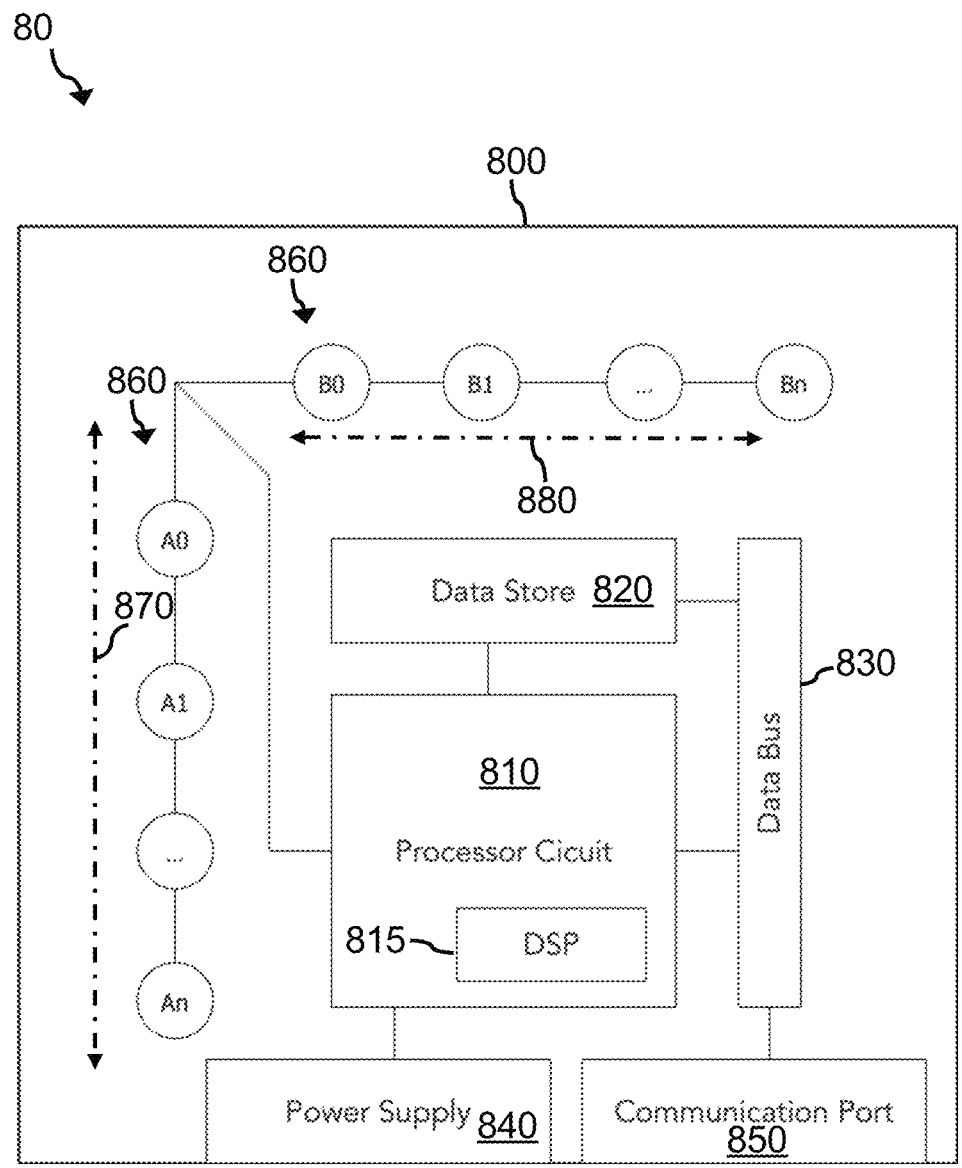
FIG. 7 is a block diagram of a motion tracking system according to an embodiment.

FIG. 7 is a block diagram of a motion tracking system 80 according to an embodiment. The motion tracking system 80 can be the same as wireless motion tracking system 420 and/or motion tracking system 100. The motion tracking system 80 includes a housing 800, a processor circuit 810, a data store 820, a data bus 830, a power supply 840, an optional communication port 850, and a plurality of RF antennas 860. The housing 800 can contain some or all components of the system 80 including the processor circuit 810, the data store 820, the data bus 830, the power supply 840, the optional communication port 850, and/or the RF antennas 860. The housing 800 can comprise plastic, ceramic, or another material. The housing 800 is preferably at least partially transparent to the RF frequency(ies) emitted and/or received by the RF antennas 850. For example, the housing 800 can provide minimal (e.g., less than 5-10%) or no attenuation of the RF signals emitted and/or received by the RF antennas 860. In some embodiments, some or all of the components can be mounted on or electrically connected to a printed circuit board. In some embodiments, the RF antennas 860 can be replaced another energy-emission device such as ultrasonic transducers.

The processor circuit 810 can comprise an integrated circuit (IC) such as a microprocessor, an application-specific IC (ASIC), or another hardware-based processor. For example, the microprocessor can comprise a central processing unit (CPU), a graphics processing unit (GPU), and/or another processor. The processor circuit 810 also includes one or more digital signal processors (DSPs) 815 that can drive the RF antennas 860. The construction and arrangement of the processor circuit 810 can be determined by the specific application and availability or practical needs of a given design. The processor circuit 810 is electrically coupled to the power supply 830 to receive power at a predetermined voltage and form. For example, the power supply 840 can provide AC power, such as from household AC power, or DC power such as from a battery. The power supply 840 can also include an inverter or a rectifier to convert the power form as necessary (e.g., from AC power to DC power or from DC power to AC power, respectively).

The optional communication port 850 can be used to send and/or receive information or data to and/or from a second device, such as a computer, a sensor (e.g., in the subject's bedroom), a server, and/or another device. The optional communication port 850 can provide a wired or wireless connection for communication with the second device. The wireless connection can comprise a LAN, WAN, WiFi, cellular, Bluetooth, or other wireless connection. In some embodiments, the optional communication port 850 can be used to communicate with multiple devices.

The data store 820 can include computer-readable memory (e.g., volatile and/or non-volatile memory) that can store data representing stored machine-readable instructions and/or data collected by the system 80 or intermediate data used by the processor circuit 810. The data bus 830 can provide a data connection between the data store 820, the processor circuit 810, and/or the optional communication port 850.

The RF antennas 860 can include or consist of one or more dedicated transmitting antennas and/or one or more dedicated receiving antennas. Additionally or alternatively, one or more of the RF antennas 860 can be a transceiver antenna (e.g., that can transmit and receive signals but preferably not simultaneously). Any receiving antenna 860 can receive a signal from any transmitting antenna 860. In one example, an antenna sweep can occur by sending a first signal from a first transmitting antenna 860, which is received by one or more receiving antenna(s) 860. Next, a second transmitting antenna 860 can send a second signal, which can be received by one or more receiving antenna(s) 860. This sweep process can continue where each transmitting antenna 860 sequentially sends a respective signal that is received by one or more receiving antenna(s) 860. Each signal can be reflected by the subject partially or fully.

The RF antennas 860 can be disposed in a suitable arrangement with respect to one another to form one or more wireless transmit-receive arrays. As illustrated, a first group or array of RF antennas 860 (A0, A1 . . . An) is placed along or parallel to a first axis 870 and a second group or array of RF antennas 860 (B0, B1 . . . Bn) is placed along or parallel to a second axis 880 that is orthogonal to the first axis 870, for example in an "L" arrangement. The first and second groups of RF antennas 860 can be configured and arranged at to capture a spatial position of the target of interest, e.g., the subject's body and the bed. It is noted that the first and second groups of RF antennas 860 can be arranged in different relative orientations to achieve the same or substantially the same result. For example, the first and second axes 860, 870 can disposed at other angles with respect to each other that are different than 90°. Alternatively, the first and second groups of RF antennas 860 can be configured in a "T" arrangement or a "+" instead of the "L" arrangement illustrated in FIG. 7.

In addition or in the alternative, one group of RF antennas 860 can be used to collect reflection and position data in the (x, y) plane, which can be defined as parallel to the floor or sleeping surface planes, and the other group of RF antennas 860 can be used to optionally collect height or elevation data regarding the third (z) axis position. In another embodiment, each group of RF antennas 860 can include one or more dedicated transmit antennas, one or more dedicated receive antennas, and/or one or more dedicated transmit antennas and one or more dedicated receive antennas. The RF antennas 860 in each group can be spaced at equal distances from each other, or they may not be, and may even be randomly spaced or distributed in the housing 800. Alternatively, those skilled in the art will understand that the system may be constructed using more than one physical device that can be distributed spatially about an indoor environment such as a bedroom, hospital room or other space, i.e., placing separate components within multiple distinct housings.

In a preferred but not limiting example, the RF antennas 860 can span a finite spatial extent which allows for localization or triangulation to determine the position of a reflecting body, e.g., the subject's body. For example, the RF antennas 860 can emit RF signals with a wavelength in a range of about 0.01 meter (i.e., about 1 cm) to about 1 meter, including any value or range therebetween. In another example, the RF radiation used may have a wavelength between the RF antennas 860 can emit RF signals with a wavelength in a range of about 1 cm to about 10 cm, including any value or range therebetween. Electromagnetic radiation waves with wavelengths greater than 1 mm are preferred, i.e., those wavelengths substantially greater than the wavelengths of visible light.

The motion tracking system 80 can be programmed, configured, and/or arranged to perform motion tracking automatically, for example using the RF antennas 860 and processing components. Therefore, the motion tracking system 80 can continuously and inexpensively monitor a human subject in an indoor environment such as a bedroom, though sometimes the present system can emit and receive wireless signals through walls, furniture or other obstructions to extend its versatility and range. Also, the motion tracking system 80 can continuously monitor, detect, and/or measure the data required to determine or estimate the TUG time for a subject under observation. Furthermore, the motion tracking system 80 can be deployed to an observation space (e.g., a subject's bedroom) in a non-obtrusive form factor such as a bedside apparatus or an apparatus inconspicuously mounted on a wall, ceiling, or fixture of the subject's room. Still further, the motion tracking system 80 does not pose the costs and privacy concerns associated with measuring TUG by another human observer or by a camera-based system.

In some embodiments, the measured TUG time can quantify or can be used to quantify an indication of disease, health, and/or treatment. For example, the measured TUG time can quantify or can be used to quantity a disease severity, a disease progression, and/or a medication effectiveness (e.g., by comparing a current TUG time after medication is administered to a past TUG time before medication is administered). In a specific example, the measured TUG time can quantify or can be used to quantity an indication of a neurological condition such as muscular dystrophy and/or facioscapulohumeral muscular dystrophy (FSHD). The measured TUG time can also quantify and/or be used to quantify an indication of whole-body health The motion tracking system 80 can be coupled to a communication network (e.g., using optional communication port 850) so that data collected may be analyzed remotely, off-line, or in real time by a human or a machine (e.g., computer, server, etc.) coupled to the network. For example, the optional communication port 850 can be used to deliver data over the network (e.g., the internet) to a server, clinical station, medical care provider, family member, or other interested party. Data collected can be archived locally in memory (e.g., data store 820) of the system 80 or may transmitted (e.g., using optional communication port 850) to a data collection or storage unit or facility over a wired or wireless communication channel or network.

A processor-implemented or processor-assisted method can be carried out automatically or semi-automatically. The processing may take place entirely on internal processing components disposed in the system 80 and/or at a remote processing location. For example, the system 80 can receive the wireless signal data and send that data to be processed remotely such as at a cloud-based server. In yet other embodiments a hybrid arrangement may be used where processing is performed at both the local device (e.g., in system 80) and remotely. Therefore, for the present purposes, unless described otherwise, the location of the processing acts is not material to most or all embodiments.

Figure 8:
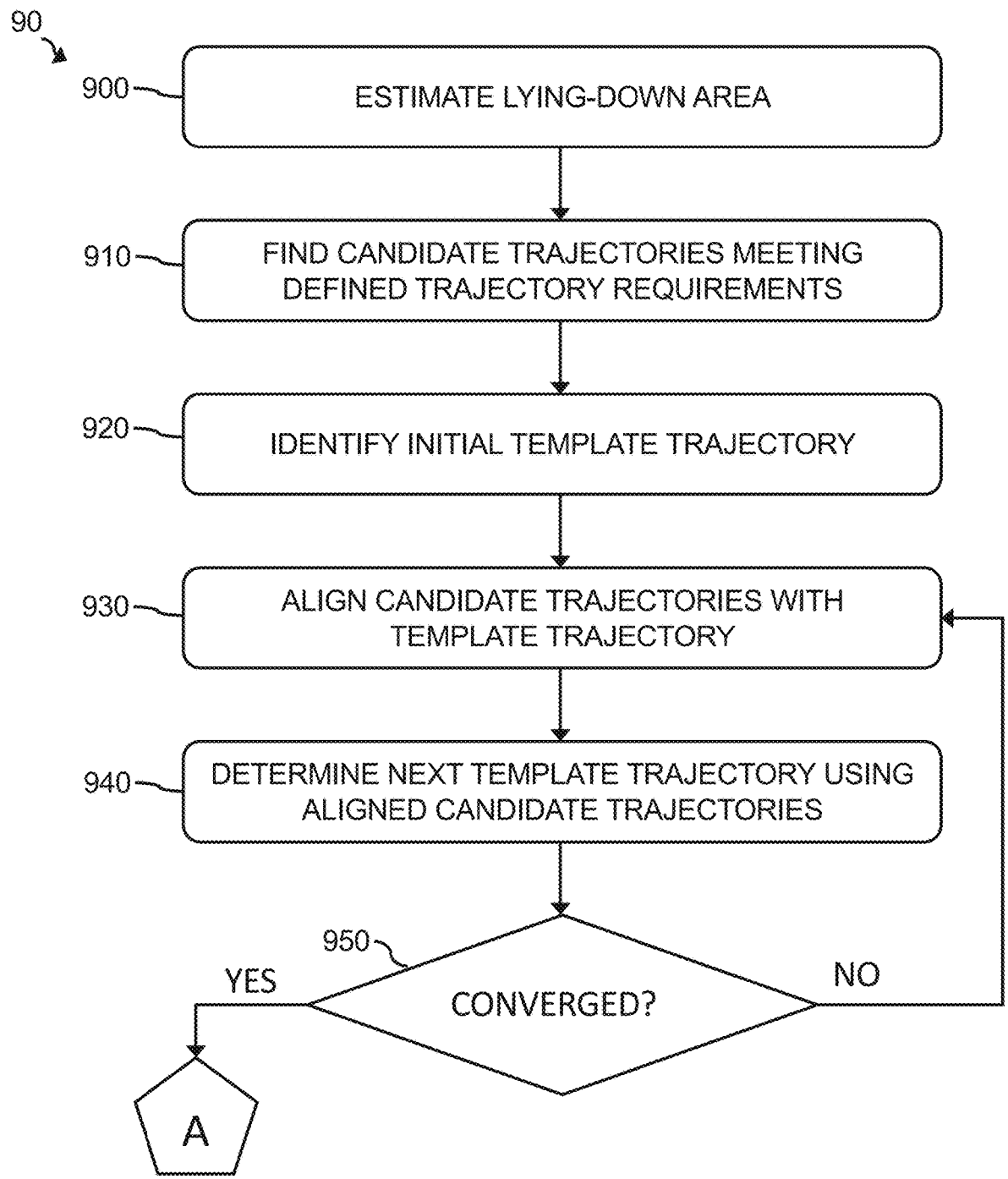
FIG. 8 is a flow chart of a method for measuring a subject's TUG according to an embodiment.
Figure 8:
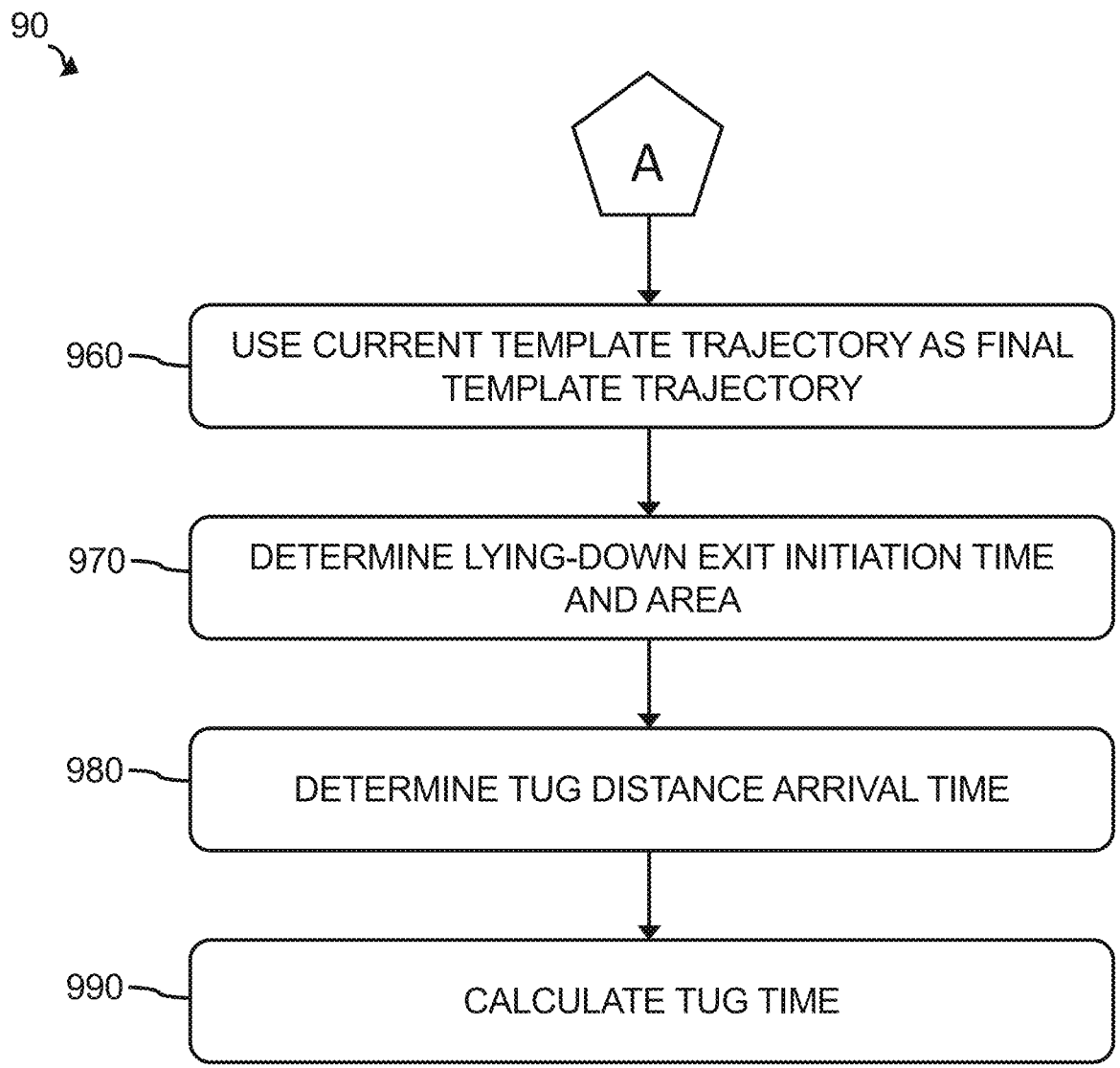

FIG. 8 is a flow chart of a method 90 for measuring a subject's TUG according to an embodiment. The method 90 can be performed using motion tracking system 100, wireless motion tracking system 420, and/or motion tracking system 80.

In step 900, the subject's sleep or lying-down area is estimated. In an aspect, every trajectory is accumulated and stored for study and analysis. The space in which the subject is found to sleep is discretized into a grid, for example a square grid with 10-cm granularity or resolution. Therefore, a matrix of 10-cm pixels can be created with a number of pixels in each dimension under study (e.g., a 100×100 matrix of pixels). The pixels are akin to a histogram that then generates a two-dimensional (or three-dimensional) heatmap which can be displayed and analyzed. In an example, at each time step or window in which the subject has remained within a given bed area for a period of time (e.g., 60 seconds) the pixel map is updated to reflect a (+1) count recording the subject's sleep in this pixel area. In an optional step, the heatmap may be smoothed using a smoothing function such as a Gaussian filter to reduce the effects of noise in the data. Additional data processing and pre-processing can be applied to the collected sleep or lying-down position data such as programmably eliminating outlier and noisy pixel data, normalizing the data by dividing by the 99.9 percentile value (or another suitable factor). Those skilled in the art will understand a variety of such techniques to apply to their collected data as needed for a given application.

In step 910, candidate trajectories are found that meet defined trajectory requirements. Finding the candidate trajectories may include filtering the trajectory data as it is measured and calculated, optionally keeping only the relevant segments of the trajectories to speed processing time and disregarding outlying portions thereof. For example, if a trajectory does not start from and exit (e.g., extend away from) the bed then it is discarded as not useful. Once a sleep or lying-down area has been defined, the system and method may eliminate potential candidate trajectories that start in the sleep or lying-down area (e.g., bed or platform) and remain in the sleep or lying-down area for a predetermined maximum time period such as at least 30 minutes, or some other time selected by the operator of the study. In addition, the system and method can eliminate potential candidate trajectories that do not remain in the bed start area for a predetermined minimum time period such as at least 1 minute. This ensures that the selected candidate trajectories belong to instances where the person has actually been in the bed for a longer period of time and they did not simply walk back and forth to the bed.

Figure 9:
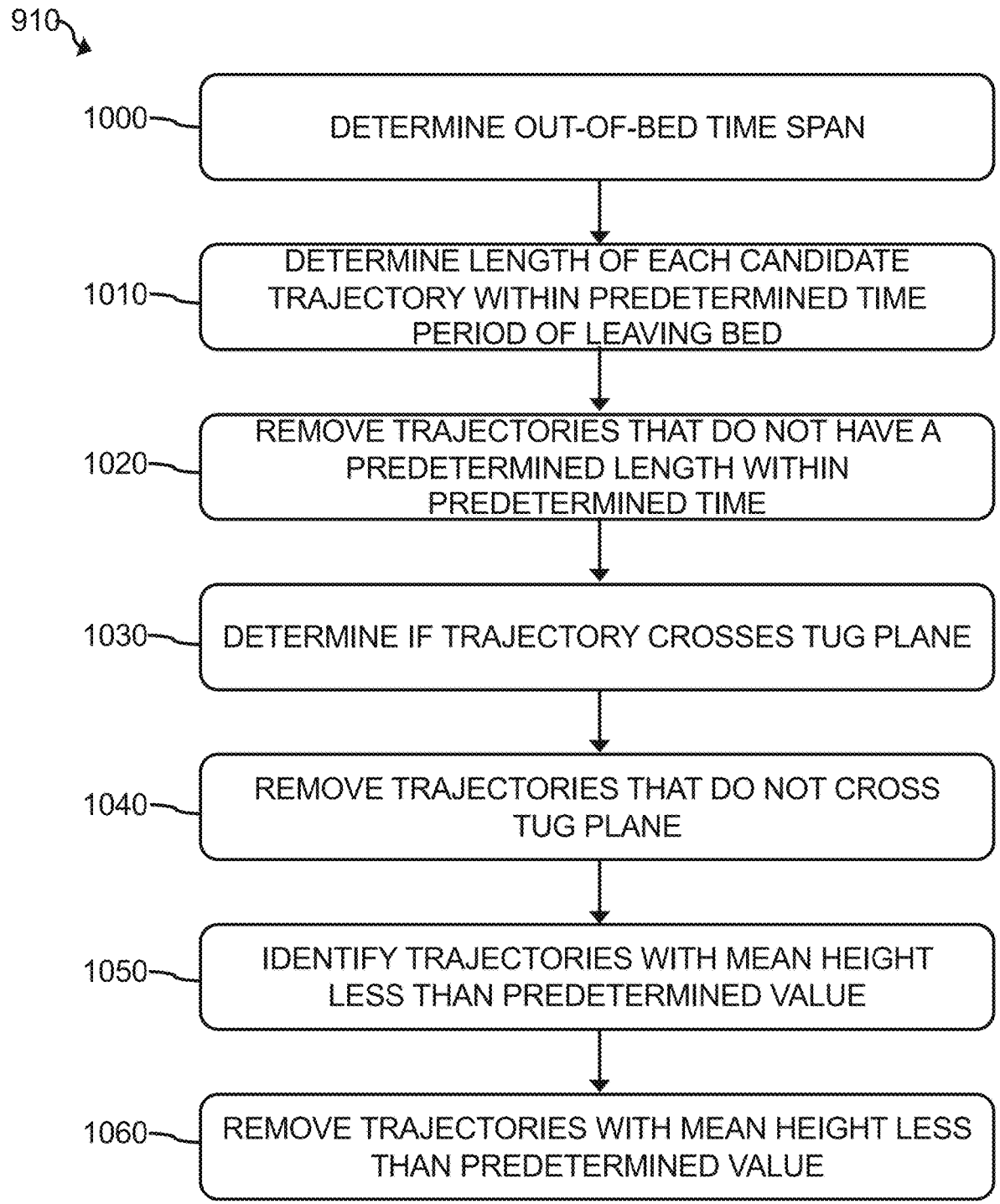
FIG. 9 is a flow chart of step 910 in FIG. 8 according to an embodiment.

FIG. 9 is a flow chart of step 910 according to an embodiment. In step 1000, the system determines the out-of-bed time span of the trajectory after leaving the bed. The out-of-bed time span can correspond to the time that the subject leaves the sleep area 430 and enters or passes through the initiation area 440 and/or exit plane 450. In step 1010, the system determines the length of each candidate trajectory for a predetermined time period after the out-of-bed time. The predetermined time period can be about 10 seconds, about 15 seconds, or another time period that can correspond to a TUG measurement. In step 1020, the system can remove all candidate trajectories that have a length, radius, or circumference, in the predetermined time period after the exit time, that is less than or equal to a predetermined length. The predetermined length can be at least 2 meters, at least 2.5 meters, or another length that can correspond to a TUG measurement.

In step 1030, the system determines whether any of the remaining candidate trajectories cross the bed plane 450, which can alternatively be a bed radius. Any candidate trajectories that do not cross the bed plane are removed in step 1040. In optional steps 1050 and 1060, any remaining trajectories that have a mean height or elevation above ground, after bed exit, that is less than a predetermined height (e.g., a mean height, z, less than or equal to 0.75 meters or another height), can be identified and removed to eliminate trajectories generated by pet movement or other potential noise.

Returning to FIG. 8, in steps 920, 930, 940 and 950 we perform an iterative algorithm, which finds the template trajectory. We can find an initial candidate template trajectory in step 920. Then, in step 930, we can align all candidate trajectories to the current candidate template trajectory. In step 940, we can find a refined version of the template trajectory based on the alignment of step 930. If the refined and aligned template trajectories have converged, the refined version is our output, otherwise we can return to step 930 with using the refined trajectory as our new template trajectory candidate.

In step 920 an initial template trajectory is identified, determined, or computed. The initial template trajectory can be used to align candidate trajectories and to extract common features therefrom. The initial template trajectory can be a random or arbitrary trajectory selected from the candidate trajectories identified in step 910 (i.e., the candidate trajectories that meet defined trajectory requirements). In other embodiments, the longest trajectory from the candidate trajectories identified in step 910 can be selected as the template trajectory.

In step 930, each of the remaining candidate trajectories is aligned with the candidate template trajectory. In some embodiments, alignment can be performed by shifting the candidate trajectories in time in order to minimize a measure of distance of the shifted candidate trajectory from the initial template trajectory while requiring each candidate trajectory to overlap with the candidate template trajectory at least a fixed length of the candidate template trajectory's length. In one example implementation one can find a parameter $\delta_i$ for every candidate trajectory candidate$_i$, which is the corresponding time offset. Given the time $\delta_i$ one can calculate the distance between each point of the candidate trajectory candidate$_{ij}$ and the candidate template trajectory. The measure of distance $D_{ij}$ could be the Euclidian distance between candidate$_{ij}$ and the closest-in-time point of the candidate template trajectory after offsetting the candidate trajectory by $\delta_i$:

$$D_{ij} = |\text{template}_{k,xy} - \text{candidate}_{ij,xy}|^2$$

Given where index k is chosen to minimize the time difference between the corresponding candidate template and candidate trajectory:

$$\underset{k}{\arg\min} |\text{template}_{k,time} - \text{candidate}_{ij,time} - \delta_i|$$

The global optimization function that is being optimized is the sum of distances of all points of all candidate trajectories:

$$\sum_{ij} D_{ij}$$

Finding the optimal time offset $\delta_i$ for every candidate trajectory can now be found using an optimization algorithm that minimizes the global optimization function using the constraint that each candidate trajectory needs to have a certain overlap with the candidate template trajectory—for example it needs to cover at least 70% of the candidate template trajectory length.

In step 940, a next refined template trajectory is determined using the aligned candidate trajectories from step 930. The refined template trajectory can be determined by calculating the mean, median, or other calculation of the x, y, and z coordinates for each aligned point in the aligned candidate trajectories in step 930.

In step 950, the system determines whether the refined and the candidate template trajectories have converged. Determining whether the refined and the candidate template trajectories have converged can comprise determining whether a measure of distance between the current and prior template trajectories is less than or equal to a maximum allowable distance. The distance between the two trajectories can be calculated on an elementwise basis by calculating the Euclidian or any other distance between every two corresponding points.

If the refined and candidate template trajectories have not converged (i.e., the distance between the refined and candidate template trajectories is greater than a maximum allowable distance), then the flow chart returns to step 930 where the candidate trajectories are aligned with the refined template trajectory in the same manner as described above in step 930. In step 940, the system determines another (e.g., second next) candidate template trajectory using the candidate trajectories that were aligned with the refined template trajectory in step 930, and the system determines whether the refined and candidate template trajectories have converged in step 950. Steps 930-950 can repeat iteratively until the current and prior template trajectories have converged.

When the current and prior template trajectories converge, the current template trajectories are used as the final template trajectory in step 960.

In some embodiments, one or more trajectories, which is a set of points in space and time tracking the subject's movement, can be aligned to a prior trajectory or aggregated ensemble of trajectories. For example, a given trajectory (e.g., the subject getting up from bed on a given morning, e.g., Tuesday) can be time-shifted with a previous trajectory (e.g., the subject getting up from bed on the prior morning, e.g., Monday). Then, on the following morning (e.g., Wednesday) that day's trajectory can be time-shifted to an aggregated, averaged, or idealized ensemble of the prior-collected trajectories. In one example, each new trajectory is time-shifted to align it with a template generated by the plurality of all of the previously collected (and optionally time-shifted) trajectories. The aligned prior-collected trajectories can be a predetermined trajectory can be considered multiple predetermined trajectories.

The above time-shifted alignment of a trajectory may be performed in a multi-dimensional (spatial) trajectory (e.g., in x and y in the plane of or parallel to the floor) by separately time-shifting or aligning a one-dimensional slice of the trajectory (e.g., along the x-axis) to align or match up or minimize its overall sum difference from the prior aggregated ensemble of x-axis sliced and aligned data. The process of creating the aggregated ensemble of trajectories results in a template trajectory, in one or more than one spatial dimension. Temporal alignment may also or instead include stretching a trajectory along one or more dimensions.

Alignment of trajectory data can also be accomplished spatially, for example by rotating a trajectory in space about one or more axes of rotation. In one example, the data may be rotated about the angular dimension if the data is collected or represented in cylindrical coordinates (e.g., by shifting the angular "theta" dimension). Rotating a trajectory in space such as in Cartesian (x, y) coordinates is also possible. In some aspects, spatially rotating or processing the trajectory data can account for a subject getting up and heading towards different initial destinations in space (e.g., walking towards the refrigerator as opposed to walking to the bathroom after getting out of bed). This alignment can be thought of as an optimization or minimization step to obtain the best template trajectory. A more consistent knowledge of the place and time of initial get-up or initiation of the getting out of bed is made possible by the present alignment and template tracking.

Figure 10:
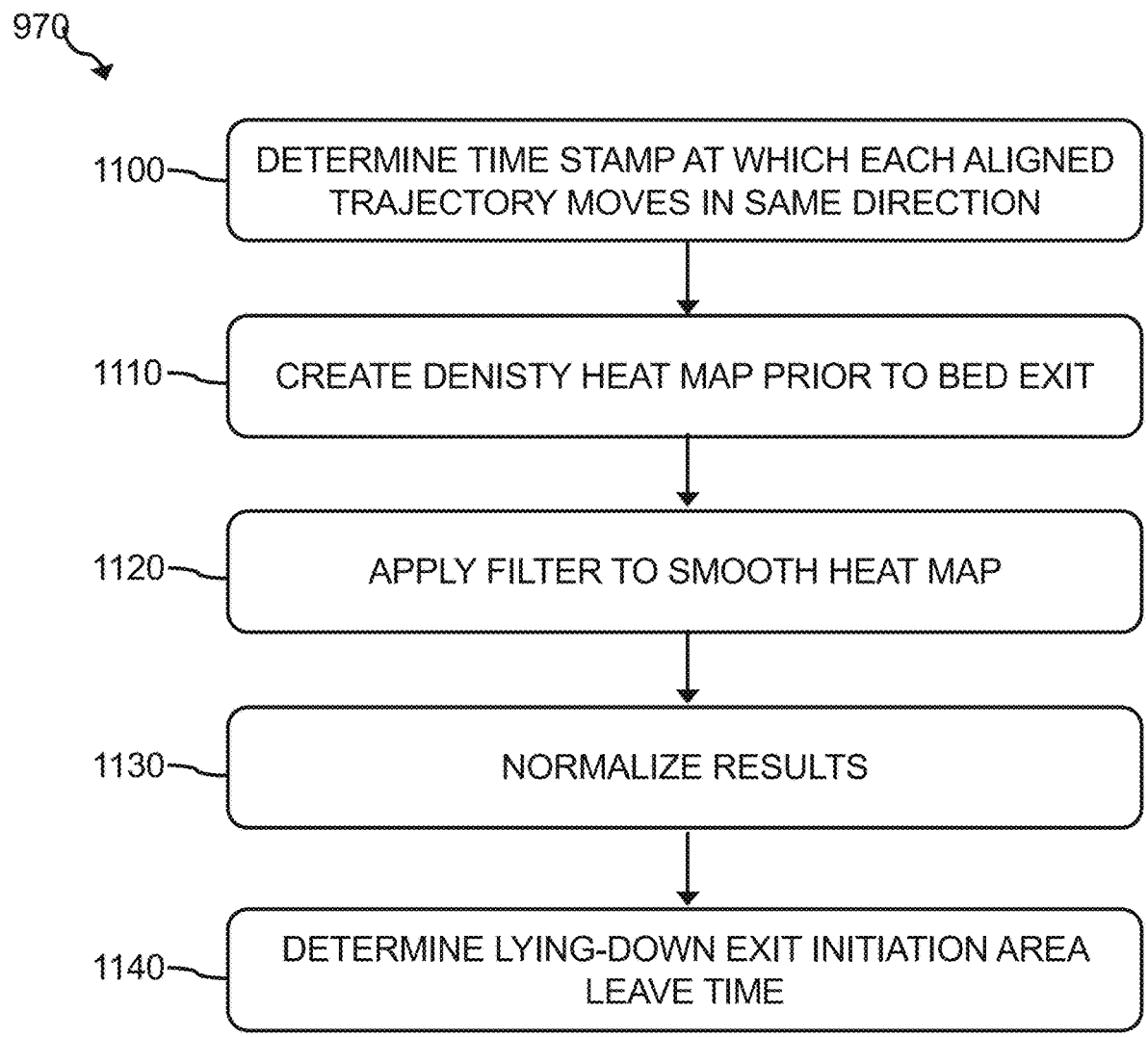
FIG. 10 is a flow chart of step 970 in FIG. 8 according to an embodiment.

In step 970, the bed exit initiation time and bed exit initiation area 440 (e.g., lying-down surface exit initiation area exit time and lying-down surface exit initiation area, respectively) are determined. In some embodiments, step 970 can be performed according to the flow chart in FIG. 10.

In step 1100 (FIG. 10), a time stamp at which each aligned candidate trajectory starts to exhibit movement in the same direction is determined. Such a timestamp can be determined, for example, by computing the sum of the displacement vectors for all aligned trajectories at each timestamp, and picking the first timestamp where the magnitude of this sum crosses a threshold. This timestamp can correspond to the bed exit initiation time (e.g., lying-down surface exit initiation area exit time), which is used as the start of the TUG measurement. The displacement vector at any timestamp is defined as the instantaneous orientation of the trajectory at that timestamp, and can, for instance, be computed by taking the difference between the positions of the trajectory at time points around that timestamp.

In step 1110, the system creates an initiation area density heatmap (e.g., a lying-down surface exit initiation area density heatmap). The density heatmap can be created using a predetermined time period (e.g., one second) before the timestamp determined in step 1100 and taking all the candidate trajectories from the predetermined period. The space can be discretized into bins, for example 10 cm by 10 cm, and for each point of the aligned candidate trajectories that is in the considered time period we add 1 to the corresponding discretized bin. In step 1120, a filter, such as a Gaussian 2D filter, is applied to smooth the density heatmap. Other filters can be used in other embodiments. For example, a 3D filter can be used when the density heatmap includes a third dimension (e.g., along the z axis). In step 1130, the filtered heatmap is normalized. Normalization can occur with respect to a maximum value of the pixels in the heatmap, or another value.

In step 1140, the bed exit initiation area leave time (lying-down surface exit initiation area leave time) is determined. For each aligned candidate trajectory, the probability is determined (e.g., by calculating a probability function) for whether the path of the aligned candidate trajectory has exited the bed exit initiation area. The filtered heatmap generated in step 1130 can be used in calculating the probability function. For each time point of the candidate trajectory, t, we can calculate the probability function $P_t$, which is the probability that the candidate trajectory is in the bed exit initiation area (e.g., lying-down surface exit initiation area at that time instance:

$$P_t = \alpha * (\text{heatmap}_{x_t, y_t} - P_{t-1})$$

where $\alpha$ is a parameter that can be adjusted. If the probability function exceeds a threshold, the patient has entered the bed initiation area and has begun the motion of exiting the bed.

Returning to FIG. 8, in step 980 the timestamp at which the trajectory is at least a certain distance or radius away from the bed can be determined. This could be, for example 2 meters away from the bed based on Euclidian distance or any other distance and distance metrics could be used. Additionally or alternatively, the system can determine timestamp at which the subject reaches (e.g., along a trajectory) a predetermined location in the room (e.g., in which the platform is located). The system can determine the time stamp at which each candidate trajectory exceeds the corresponding distance from the bed or reaches the predetermined location in the room. The distance from the bed can be measured along a straight path or a non-linear path. The measured trajectory along which the subject travels can be a straight path or a substantially/sufficiently straight path (e.g., based on statistical analysis of the trajectory). Additionally or alternatively, the subject can move at a consistent pace (e.g., plus or minus 10% of an average speed) along the measured trajectory. The measured trajectory having a straight path and/or the subject having a consistent pace can be prerequisites for the system to determine whether to stop the TUG timer to determine the timestamp at which the subject has travelled for a predetermined distance, for a predetermined time period, and/or to a predetermined location, which can be an absolute location or a relative location with respect to the platform.

Additionally or alternatively, in step 980 the timestamp at which the subject has travelled from the platform for a predetermined time period and/or the timestamp at which the subject has travelled along a predetermined trajectory for a predetermined time period can be determined.

In step 990, the TUG time is calculated. The TUG time can be determined by calculating the difference between the timestamp at which the trajectory is at least a certain distance away from the bed (e.g., determined in step 980) and the bed exit initiation time (e.g., determined in step 970). The TUG time can be displayed on a display that is in electrical communication with the system and/or stored in the system.

In an optional aspect, the system may be configured or programmed to detect alarm conditions based on the data collected regarding the human subject's behavior, movement or other conditions sensed by the system. Alarm conditions may set off an audible and/or visual alarm indicator at a local or remote station. Furthermore, alarm conditions may be transmitted over a network to an external (human or machine) monitor or supervisor, e.g., over the internet or over a cellular or land-line telephone. An example alarm might be detecting that the subject has taken unusually long to exit the bed, compared to either a prior average computed for that subject, or an absolute threshold. Another alarm can be based on a lack of movement of the subject over a predetermined time period. Another alarm can be based on a sudden movement of the subject, such as a sudden elevational change of the subject, which may indicate that the subject has fallen.

While this system and method can be applied to measurements of TUG specific to bed exit time, which may be useful in diagnosing or evaluating the severity of conditions such as muscular dystrophy, the invention is not so limited. The same or equivalent and corollary systems and methods may be employed to study other conditions of a subject.

Certain embodiments are directed to a system and method for measuring the activity completion time such as a TUG, O-TUG, C-TUG (i.e., Cognitive TUG where the subject performs a cognitive task while performing the TUG), or E-TUG (i.e., Expanded TUG where each TUG subtask is evaluated or timed separately. Specifically, in some embodiments, wireless wave signals having a wavelength greater than 1 millimeter (whether electromagnetic or acoustic or otherwise) are reflected in a transmit-receive environment to detect the presence and movement of a subject. The results of transmission and reception of the wireless signals is processed and analyzed to compute spatial dynamics of the subject under study with respect to zones defined in space such as sleep areas and bed exit initiation areas (e.g., lying-down surface exit initiation areas) and terminal distances a given distance away from the bed or exit area.

Further steps may include correlating the TUG or related bed exit measurements with a clinical or health condition including progressive muscle dystrophy diseases and aging related degeneration.

In some aspects the wireless signals are capable of passing through solid obstructions, objects, walls and other physical barriers in the environment of the measurement device and/or the subject. In other aspects the system and method include alignment of a plurality of position trajectories in time and space and may employ further steps of filtering and minimization to achieve a template trajectory characterizing the bed exit of a particular subject under investigation.

In yet other aspects the system comprises hardware including transmit/receive arrays having a finite spatial extent over a dimension of said arrays and including a plurality of array elements (e.g., antennas, transducers) which can spatially locate a subject or part thereof in space, repeatedly in time, so as to accumulate spatial dynamics of the subject in a trace or trajectory.

The present invention should not be considered limited to the particular embodiments described above. Various modifications, equivalent processes, as well as numerous structures to which the present invention may be applicable, will be readily apparent to those skilled in the art to which the present invention is directed upon review of the present disclosure. The above-described embodiments may be implemented in numerous ways. One or more aspects and embodiments involving the performance of processes or methods may utilize program instructions executable by a device (e.g., a computer, a processor, or other device) to perform, or control performance of, the processes or methods.

In this respect, various inventive concepts may be embodied as a non-transitory computer readable storage medium (or multiple non-transitory computer readable storage media) (e.g., a computer memory of any suitable type including transitory or non-transitory digital storage units, circuit configurations in Field Programmable Gate Arrays or other semiconductor devices, or other tangible computer storage medium) encoded with one or more programs that, when executed on one or more computers or other processors, perform methods that implement one or more of the various embodiments described above. When implemented in software (e.g., as an app), the software code may be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer, as non-limiting examples. Additionally, a computer may be embedded in a device not generally regarded as a computer but with suitable processing capabilities, including a Personal Digital Assistant (PDA), a smartphone or any other suitable portable or fixed electronic device.

Also, a computer may have one or more communication devices, which may be used to interconnect the computer to one or more other devices and/or systems, such as, for example, one or more networks in any suitable form, including a local area network or a wide area network, such as an enterprise network, and intelligent network (IN) or the Internet. Such networks may be based on any suitable technology and may operate according to any suitable protocol and may include wireless networks or wired networks.

Also, a computer may have one or more input devices and/or one or more output devices. These devices can be used, among other things, to present a user interface. Examples of output devices that may be used to provide a user interface include printers or display screens for visual presentation of output and speakers or other sound generating devices for audible presentation of output. Examples of input devices that may be used for a user interface include keyboards, and pointing devices, such as mice, touch pads, and digitizing tablets. As another example, a computer may receive input information through speech recognition or in other audible formats.

The non-transitory computer readable medium or media may be transportable, such that the program or programs stored thereon may be loaded onto one or more different computers or other processors to implement various one or more of the aspects described above. In some embodiments, computer readable media may be non-transitory media.

It should be appreciated that, according to one aspect, one or more computer programs that when executed perform methods of the present application need not reside on a single computer or processor, but may be distributed in a modular fashion among a number of different computers or processors to implement various aspects of the present application.

Computer-executable instructions may be in many forms, such as program modules, executed by one or more computers or other devices. Generally, program modules include routines, programs, objects, components, data structures, etc. that perform particular tasks or implement particular abstract data types. The functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

Thus, the present disclosure and claims include new and novel improvements to existing methods and technologies, which were not previously known nor implemented to achieve the useful results described above. Users of the present method and system will reap tangible benefits from the functions now made possible on account of the specific modifications described herein causing the effects in the system and its outputs to its users. It is expected that significantly improved operations can be achieved upon implementation of the claimed invention, using the technical components recited herein.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

What is claimed is:

1. A method for wireless detection of a subject rising from a rest state, comprising:
   a. producing transmitted wireless signals from one or more transmitting antennas;
   b. receiving reflected wireless signals at one or more receiving antennas, the reflected wireless signals being reflected from the subject partially or fully;
   c. processing the reflected wireless signals in a computer to estimate a lying-down area of the subject, the computer including a microprocessor and memory electrically coupled to the microprocessor;
   d. processing the reflected wireless signals in the computer to determine a plurality of candidate trajectories of the subject, each candidate trajectory corresponding to a movement of the subject over a time period;
   e. aligning the candidate trajectories, in the computer, with an initial template trajectory;
   f. determining, in the computer, a new template trajectory using the aligned candidate trajectories;
   g. determining, in the computer, whether the new template trajectory is within a predetermined distance of the initial template trajectory;
   h. when the new template trajectory is greater than the predetermined distance of the initial template trajectory:
      replacing the new template trajectory with the initial template trajectory; and
      repeating steps e-g until the new template trajectory is within the predetermined distance of the initial template trajectory;
   i. when the new template trajectory is less than or equal to the predetermined distance of the initial template trajectory:
      saving the new template trajectory as a final template trajectory;
      determining, in the computer, a lying-down surface exit initiation area using the aligned candidate trajectories;
      determining, in the computer, a lying-down surface exit initiation area exit time for each aligned candidate trajectory using the lying-down surface exit initiation area;
      determining, in the computer, a time-up-and-go (TUG) plane entry time for each aligned candidate trajectory; and
      calculating, in the computer, a TUG time based on a difference between the TUG plane entry time and the lying-down surface exit initiation area exit time.

2. The method of claim 1, wherein the one or more transmitting antennas are configured to transmit wireless signals having a wavelength greater than 1 mm.

3. The method of claim 1, wherein:
   the one or more transmitting antennas comprise a plurality of the transmitting antennas,
   the one or more receiving antennas comprise a plurality of the receiving antennas, and
   the transmitting and receiving antennas are arranged along two orthogonal axes.

4. The method of claim 3, wherein the transmitting antennas and the receiving antennas are evenly spaced along the two orthogonal axes.

5. The method of claim 1, further comprising determining whether the candidate trajectories satisfy one or more predefined trajectory requirements.

6. The method of claim 5, wherein the predefined trajectory requirement(s) include that the candidate trajectory originates at a lying-down surface.

7. The method of claim 6, wherein the predefined trajectory requirement(s) include that the candidate trajectory extends away from the lying-down surface.

8. The method of claim 5, wherein the predefined trajectory requirement(s) include that the candidate trajectory remains on the lying-down surface for less than a predetermined maximum time period.

9. The method of claim 1, wherein the step of determining a lying-down surface exit initiation area exit time using the final template trajectory and the lying-down surface exit initiation area, comprises determining a time stamp at which each aligned candidate trajectory moves in a same direction.

10. The method of claim 9, wherein the step of determining a time stamp at which each aligned candidate trajectory moves in a same direction comprises:
    computing a sum of displacement vectors for the aligned candidate trajectories at respective timestamps; and
    selecting a first timestamp where a magnitude of the sum of the displacement vectors is greater than a threshold value.

11. A system for wireless detection of a subject rising from a rest state, comprising:
    one or more transmitting antennas;
    one or more receiving antennas;
    a microprocessor electrically coupled to the one or more transmitting and the one or more receiving antennas;
    a power supply electrically coupled to the microprocessor; and
    computer-readable memory electrically coupled to the microprocessor, the computer-readable memory including computer-readable instructions that, when executed by the microprocessor, cause the microprocessor to:
       a. produce transmitted wireless signals from the one or more transmitting antennas;
       b. receive reflected wireless signals from the one or more receiving antennas, the reflected wireless signals being reflected from the subject partially or fully;
       c. process the reflected wireless signals to estimate a lying-down area of the subject;
       d. process the reflected wireless signals to determine a plurality of candidate trajectories of the subject, each candidate trajectory corresponding to a movement of the subject over a time period;
       e. align the candidate trajectories with an initial template trajectory;
       f. determine a new template trajectory using the aligned candidate trajectories;
       g. determine whether the new template trajectory is within a predetermined distance of the initial template trajectory;
       h. when the new template trajectory is greater than the predetermined distance of the initial template trajectory:
          replace the new template trajectory with the initial template trajectory; and
          repeat steps e-g until the new template trajectory is within the predetermined distance of the initial template trajectory;

i. when the new template trajectory is less than or equal to the predetermined distance of the initial template trajectory:
    save the new template trajectory as a final template trajectory;
    determine a lying-down surface exit initiation area using the aligned candidate trajectories;
    determine a lying-down surface exit initiation area exit time for each aligned candidate trajectory using the lying-down surface exit initiation area;
    determine a time-up-and-go (TUG) plane entry time for each aligned candidate trajectory; and
    calculate a TUG time based on a difference between the TUG plane entry time and the lying-down surface exit initiation area exit time.

12. The system of claim 11, further comprising a communication port operatively coupled to the microprocessor.

13. The system of claim 12, wherein the communication port is configured to communicate with an external device over a communication network.

14. The system of claim 11, wherein:
the one or more transmitting antennas comprise a plurality of the transmitting antennas,
the one or more receiving antennas comprise a plurality of the receiving antennas, and
the transmitting and receiving antennas are arranged along two orthogonal axes.

15. The system of claim 14, wherein the transmitting antennas and the receiving antennas are evenly spaced along the two orthogonal axes.

16. A method for wireless detection of a subject rising from a rest state, comprising:
producing transmitted wireless signals from one or more transmitting antennas;
receiving reflected wireless signals at one or more receiving antennas, the reflected wireless signals being reflected partially or fully from the subject while the subject transitions from a lying-down position on a platform to a travelling position;
processing the reflected wireless signals in a computer to repeatably measure a position of the subject;
identifying, with the computer, a change in the position of the subject that initiates a transition to leave the platform;
starting a time-up-and-go (TUG) timer, with the computer, when the subject initiates the transition to leave the platform; and
stopping the TUG timer, with the computer, when the subject (a) has travelled a predetermined distance from the platform, (b) has travelled from the platform along a predetermined trajectory for a predetermined time period, or (c) has reached a predetermined location, the predetermined location comprising an absolute location or a relative location with respect to the platform,
wherein the TUG timer indicates a TUG time.

17. The method of claim 16, wherein the change in the position of the subject that initiates the transition to leave the platform is related to a position of the subject entering a pre-determined exit initiation area.

18. The method of claim 17, further comprising determining a quantified measure of a disease severity, a disease progression, and/or a medication effectiveness using the TUG time.

19. The method of claim 16, further comprising determining a quantified measure of a disease severity, a disease progression, and/or a medication effectiveness using the TUG time.

20. The method of claim 16, wherein:
the one or more transmitting antennas comprise a plurality of the transmitting antennas,
the one or more receiving antennas comprise a plurality of the receiving antennas, and
the transmitting and receiving antennas are arranged along two orthogonal axes.

21. The method of claim 16, further comprising stopping the TUG timer only when (a) a measured trajectory of the subject follows a straight path or (b) the subject moves along the measured trajectory at a consistent pace.

* * * * *